(12) United States Patent
Browning et al.

(10) Patent No.: US 7,731,963 B2
(45) Date of Patent: Jun. 8, 2010

(54) TWEAK RECEPTOR AGONISTS AS ANTI-ANGIOGENIC AGENTS

(75) Inventors: Jeffrey Browning, Brookline, MA (US); Linda Burkly, West Newton, MA (US); Aniela Jakubowski, Arlington, MA (US); Timothy Zheng, Boston, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 11/725,870

(22) Filed: Mar. 20, 2007

(65) Prior Publication Data
US 2008/0008714 A1    Jan. 10, 2008

Related U.S. Application Data

(63) Continuation of application No. 10/380,611, filed as application No. PCT/US01/28451 on Sep. 12, 2001, now Pat. No. 7,208,151.

(60) Provisional application No. 60/232,355, filed on Sep. 14, 2000.

(51) Int. Cl.
*A61K 39/395* (2006.01)
(52) U.S. Cl. .............. 424/133.1; 424/134.1; 424/143.1; 424/155.1
(58) Field of Classification Search ........................ None
See application file for complete search history.

(56) References Cited

U.S. PATENT DOCUMENTS

| | | | |
|---|---|---|---|
| 4,777,245 A | 10/1988 | Foung et al. |
| 5,073,492 A | 12/1991 | Chen et al. |
| 5,858,991 A | 1/1999 | Hellerqvist et al. |
| 6,207,642 B1 | 3/2001 | Wiley |
| 6,448,042 B1 | 9/2002 | Greene |
| 6,492,123 B1 | 12/2002 | Holliger et al. |
| 6,544,761 B2 | 4/2003 | Greene et al. |
| 6,608,048 B2 | 8/2003 | Tsou et al. |
| 6,727,225 B2 | 4/2004 | Wiley |
| 6,824,773 B2 | 11/2004 | Wiley |
| 6,943,146 B2 | 9/2005 | Jakubowski et al. |
| 7,067,475 B2 | 6/2006 | Cerretti et al. |
| 7,074,408 B2 | 7/2006 | Fanslow, III et al. |
| 7,087,725 B2 | 8/2006 | Browning et al. |
| 7,109,298 B2 | 9/2006 | Browning et al. |
| 7,129,061 B1 | 10/2006 | Browning et al. |
| 7,208,151 B2 | 4/2007 | Browning et al. |
| 2002/0004041 A1 | 1/2002 | Albert et al. |
| 2002/0042368 A1 | 4/2002 | Fanslow et al. |
| 2003/0100074 A1 | 5/2003 | Yu et al. |
| 2003/0148314 A1 | 8/2003 | Berger et al. |
| 2003/0162712 A1 | 8/2003 | Cerretti et al. |
| 2003/0170228 A1 | 9/2003 | Ashkenazi et al. |
| 2003/0198640 A1 | 10/2003 | Yu et al. |
| 2003/0211096 A1 | 11/2003 | Ashkenazi et al. |
| 2003/0211993 A1 | 11/2003 | Jakubowski et al. |
| 2003/0216546 A1 | 11/2003 | Tykocinski |
| 2003/0228305 A1 | 12/2003 | Frantz et al. |
| 2004/0014176 A1 | 1/2004 | Ashkenzai et al. |
| 2004/0018170 A1 | 1/2004 | Shirwan |
| 2004/0033495 A1 | 2/2004 | Murray et al. |
| 2004/0038349 A1 | 2/2004 | Hilbert et al. |
| 2004/0047854 A1 | 3/2004 | Black et al. |
| 2004/0076955 A1 | 4/2004 | Mack et al. |
| 2004/0091473 A1 | 5/2004 | DuBose et al. |
| 2004/0175744 A1 | 9/2004 | Hu et al. |
| 2004/0253610 A1 | 12/2004 | Wiley |
| 2005/0008636 A1 | 1/2005 | Rennert |
| 2005/0054047 A1 | 3/2005 | Wiley |
| 2005/0054568 A1 | 3/2005 | Ling et al. |
| 2005/0181375 A1 | 8/2005 | Aziz et al. |
| 2005/0208046 A1 | 9/2005 | Kim et al. |
| 2005/0208500 A1 | 9/2005 | Erlander et al. |
| 2006/0084143 A1 | 4/2006 | Wiley |
| 2006/0127397 A1 | 6/2006 | Strittmatter |
| 2007/0110745 A1 | 5/2007 | Rennert |
| 2007/0280940 A1 | 12/2007 | Winkles et al. |

FOREIGN PATENT DOCUMENTS

| | | |
|---|---|---|
| WO | WO 96/18725 | 6/1996 |
| WO | WO 98/05783 | 2/1998 |
| WO | WO 98/35061 | 8/1998 |
| WO | WO 98/55508 | 12/1998 |
| WO | WO 99/11791 | 3/1999 |
| WO | WO 99/19490 | 4/1999 |
| WO | WO 99/59614 | 11/1999 |
| WO | WO 99/61471 | 12/1999 |
| WO | WO 00/37638 | 6/2000 |
| WO | WO 00/42073 | 7/2000 |
| WO | WO 01/45730 | 6/2001 |
| WO | WO 01/53486 | 7/2001 |
| WO | WO 01/85193 | 11/2001 |
| WO | WO 03/086311 | 10/2003 |
| WO | WO 2006047172 | 5/2006 |
| WO | WO 2006096487 | 9/2006 |
| WO | WO 2006125632 | 11/2006 |
| WO | WO 2006130429 | 12/2006 |
| WO | WO 2009/140177 A2 * | 11/2009 |

OTHER PUBLICATIONS

Schnieder et al. TWEAK can induce cell death via endogenous TNF and TNF receptor 1. Eur J Immunol. Jun. 1999;29(6):1785-92.*

(Continued)

*Primary Examiner*—Maher M Haddad
(74) *Attorney, Agent, or Firm*—Fish & Richardson P.C.

(57) ABSTRACT

The present invention relates to methods of modulating angiogenesis and inhibiting tumor progression by using TWEAK receptor (Fn14) agonists. In particular, methods for inhibiting angiogenesis are disclosed.

33 Claims, 12 Drawing Sheets

OTHER PUBLICATIONS

Salloum et al., NM-3, an isocoumarin, increases the antitumor effects of radiotherapy without toxicity. Cancer Res. Dec. 15, 2000;60(24):6958-63.*

Abbas AK et al. (eds), Chapter Fifteen, "Immunity to Microbes", *Cellular and Molecular Immunology*, Philadelphia: WB Saunders Co. pp. 302-314 (1991).

Abbas AK et al. (eds), Chapter One, "General Properties of Immune Responses", Introduction to Immunology, *Cellular and Molecular Immunology*, Philadelphia: WB Saunders Co. pp. 4-12 (1991).

Ashkenazi and Dixit, "Death Receptors: Signaling and Modulation", *Science*, vol. 281, pp. 1305-1308 (1998).

Bach-Elias et al., "Presence of autoantibodies against small nuclear ribonucleoprotein epitopes in Chagas' patients' sera", *Parasitol. Res.*, vol. 84, pp. 196-799 (1998).

Browning et al, "Characterization of surface lymphotoxin forms" *J. Immunol*, 154:33-46 (1995).

Cassiano et al., "Molecular Cloning of a Novel Receptor for TWEAK", *Scand. J. Immunol.* 51 (Supp. 1) 1-111, 2001.

Chaplin and Fu, "Cytokine regulation of secondary lymphoid organ development", *Current Opinion in Immunology*, vol. 10, pp. 288-297 (1998).

Chicheportiche et al. "Proinflammatory activity of TWEAK on human dermal fibroblasts and synoviocytes: blocking and enhancing effects of anti-TWEAK monoclonal antibodies." *Arthritis Res.* 2002;4(2):126-33. Epub Nov. 9, 2001.

Chicheportiche et al., "Down-regulated expression of TWEAK mRNA in acute and chronic inflammatory Pathologies", *Biochem Biophys Res Commun.*, Dec. 9;279(1):162-5 (2000).

Chicheportiche et al., "TWEAK, a new secreted ligand in the tumor necrosis factor family that weakly induces apoptosis." *J Biol Chem.*, 272(51):32401-10, (Dec. 19, 1997).

Colman PM, "Effects of amino acid sequence changes on antibody-antigen interactions," *Res. Immunol.* 145(1):33-36 (1994).

Dallman, "Cytokines and transplantation: Th1/Th2 regulation of the immune response to solid organ transplants in the adult", *Current Opinion in Immunology*, vol. 7, pp. 632-638 (1995).

De Wit et al., "Preferential Activation of Th2 Cells in Chronic Graft-versus-Host Reaction", *The Journal of Immunology*, col. 150 (2), pp. 361-366 (1993).

Desplat-Jégo et al., "TWEAK is expressed by glial cells, induces astrocyte proliferation and increases EAE severity," *Journal of Neuroimmunology*, 133:116-123 (2002).

Donohue et al., "TWEAK Is an Endothelial Cell Growth and Chemotactic Factor That Also Potentiates FGF-2 and VEGF-A Mitogenic Activity," *Arterioscler. Thromb. Vasc. Biol.*, 23:594-600 (2003).

Durie et al., "Antibody to the Ligand of CD40, gp39, Blocks the Occurrence of the Acute and Chronic Forms of Graft-vs-Host Disease", *J. Clin. Invest.*, vol. 94, pp. 1333-1338 (1994).

Feng et al., "The Fn 14 Immediate-Early Response Gene Is Induced During Liver Regeneration and Highly Expressed in Both Human and Murine Hepatocellular Carcinomas," *American Journal of Pathology*, 156(4):1253-1261 (Apr. 2000).

Ferrara et al., "The Biology of Vascular Endothelial Growth Factor," *Endocr. Rev.*, 18(1):4-25 (1997).

Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor, Blr-1", *J. Exp. Med.*, vol. 188, pp. 297-304 (1998).

Grewal and Flavell, "The CD40 Ligand", *Immunol. Res.*, vol. 16, pp. 59-70 (1997).

Grewal and Flavell, "The Role of CD40 Ligand in Costimulation and T-Cell Activation", *Immunol. Rev.*, vol. 153, pp. 85-106 (1996).

Hahm et al., "TWEAK overexpression induces hyperplasia in liver and kidney," *FASEB J.*, Abstract #471.5, vol. 17, No. 4-5 (Mar. 2003).

Han et al., "Identification of Differentially Expressed Genes in Pancreatic Cancer Cells Using cDNA Microarray," *Cancer Research*, 62:2890-2896 (May 15, 2002).

Ho et al., "Soluble Tumor Necrosis Factor-Like Weak Inducer of Apoptosis Overexpression in HEK293 Cells Promotes Tumor Growth and Angiogenesis in Athymic Nude Mice," *Cancer Research*, 64:8968-8972 (Dec. 15, 2004).

Jakubowski et al., "TWEAK induces liver progenitor cell proliferation," *J. Clin. Invest.*, 115(9):2330-2340 (Sep. 2005).

Jakubowski, "Dual Role for TWEAK in angiogenic regulation" *J. Cell Science*, 115:267-274 (2002).

Jakubowski,, "TWEAK Synergizes with Basis Fibroblast Growth Factor to Induce Endothelial Cell Proliferation, Migration and Lumen Morphogenesis", *Scand. J. Immunol.*, 51:Sup. 1:62 (2000).

Kaduka et al., "TWEAK mediates anti-tumor effect of tumor-infiltrating macrophage," *Biochemical and Biophysical Research Communications*, 331:384-390 (2005).

Kalled et al., "Anti-CD40 Ligand Antibody Treatment of $SNF_1$ Mice with Established Nephritis: Preservation of Kidney Function", *J. Immunol.*, vol. 160, pp. 2158-2165 (1998).

Kaplan et al., "Th2 Lymphocytes Kill Antigen Presenting Macrophages Through a TWEAK Dependant Pathway", *J. Of Investigative Medicine*, vol. 46:287A (1998).

Kaplan et al., "The Apoptotic Ligands TRAIL, TWEAK, and Fas Ligand Mediate Monocyte Death Induced by Autologous Lupus T Cells," *The Journal of Immunology*, 169:6020-6029 (2002).

Kawakita et al., "Functional expression of TWEAK in human hepatocellular carcinoma: possible implication in cell proliferation and tumor angiogenesis," *Biochemical and Biophysical Research Communications*, 318:726-733 (2004).

Kirk et al., "CTLA4-Ig and anti-CD40 ligand prevent renal allograft rejection in primates", *Proc. Natl. Acad. Sci. USA*, vol. 94, pp. 8789-8794 (1997).

Kogan et al., A single amino acid residue can determine the ligand specificity of E-Selectin, *J. Biol. Chem.* 270:14047-14055 (1995).

Krenger and Farrara, "Graft-versus-Host Disease and the Th1/Th2 Paradigm", *Immunol. Res.*, vol. 15, pp. 50-73 (1996).

Lenchow et al., "Differential Effects of Anti-B7-1 and Anti-B7-2 Monoclonal Antibody Treatment on the Development of Diabetes in the Nonobese Diabetic Mouse", *J. Exp. Med.*, vol. 181, pp. 1145-1155 (1995).

Lynch et al., "TWEAK induces angiogenesis and proliferation of endothelial cells", *J Biol Chem.*, 274 (13):8455-59 (Mar. 26, 1999).

Lynch et al., "Tweak Induces Proliferation in Endothelial Cells and Substitutes for EGF and Hydrocortisone in Culture", *Interferon Cytokine Res.*, vol. 18, A-46 (1998).

Mackay and Browning, "Turning off follicular dendritic cells", *Nature*, vol. 395, pp. 26-27 (1998).

Marsters et al., "Identification of a ligand for the death-domain-containing receptor Apo3", *Current Biology*, vol. 8, pp. 525-528 (1998).

Meighan-Mantha et al., "The Mitogen-inducible Fn14 Gene Encodes a Type I Transmembrane Protein that Modulates Fibroblast Adhesion and Migration" *J. Biol. Chem.*, 274: 33166-33176 (Nov. 1999).

Michaelson et al., "Tweak induces mammary epithelial branching morphogenesis," *Oncogene*, 24:2613-2624 (2005).

Mohan et al., "Interaction Between CD40 and Its Ligand gp39 in the Development of Murine Lupus Nephritis[1]", J. Immunol., vol. 154, pp. 1470-1480 (1995).

Nagata, "Apoptosis by Death Factor" *Cell* 88:355-365, (1997).

Nakayama et al., "Fibroblast Growth Factor-Inducible 14 Mediates Multiple Pathways of TWEAK-Induced Cell Death," *The Journal of Immunology*, 170:341-348 (2003).

Nakayama et al., "Involvement of TWEAK in Interferon γ-stimulated Monocyte Cytotoxicity," *J. Exp. Med*, 192(9):1373-1379 (Nov. 6, 2000).

Ngo et al., "Computational complexity, protein structure prediction, and the Levinthal paradox", *The Protein Folding Problem*, Chapter 14, pp. 435-508 (1994).

Pavco et al., "Antitumor and Antimetastatic Activity of Ribozymes Targeting the Messenger RNA of Vascular Endothelial Growth Factor Receptors," *Clin. Cancer Res.*, 6:2094-2103 (2000).

Pepper MS et al., "Biphasic effect of transforming growth factor-beta 1 on in vitro angiogenesis", *Exp Cell Res.*, 204(2):356-63 (Feb. 1993).

Saas et al., "TWEAK Stimulation of Astrocytes and the Proinflammatory Consequences," *GLIA*, 32:102-107 (2000).

Shaw et al., "Preferential transformation of human neuronal cells by human adenoviruses and the origin of HEK 293 cells," *FASEB J.*, express article 10.1096/fj.01-0995fje, 19 pages (Apr. 10, 2002).

Tibbetts et al., "Cardiac Antigen-Specific Autoantibody Production is Associated with Cardiomyopathy in *Trypansoma* cruzi-Infected Mice[1]", *J. Immunol.*, vol. 152, pp. 1493-1499 (1994).

Toogood et al., "The Immune Response Following Small Bowel Transplantation", *Transplantation*, vol. 62(6), pp. 851-855 (1996).

Tran et al., "The Human Fn14 Receptor Gene Is Up-Regulated in Migrating Glioma Cells in Vitro and Overexpressed in Advanced Glial Tumors," *Am. J. Pathol.*, 162(4):1313-1321 (Apr. 2003).

Tran et al., "The Tumor Necrosis Factor-like Weak Inducer of Apoptosis (TWEAK)-Fibroblast Growth Factor-inducible 14 (Fn14) Signaling System Regulates Glioma Cell Survival via NFκB Pathway Activation and BCL-$X_1$/BCL-W Expression," *J. Biol. Chem.*, 280(5):3483-3492 (Feb. 4, 2005).

Ward et al., "Blocking of Adhesion Molecules in vivo as anti-inflammatory therapy", *Ther. Immunol.*, vol. 1(3), pp. 165-171 (1994).

Wiley et al., "A Novel TNF Receptor Family Member Binds TWEAK and Is Implicated in Angiogenesis," *Immunity*, 15:837-846 (Nov. 2001).

Wiley et al., "Identification and Characterization of a New Member of the TNF Family that induces Apoptosis", *Immunity* 3:673-682 (1995).

Wiley et al., "TWEAK, a member of the TNF superfamily, is a multifunctional cytokine that binds the TweakR/Fn14 receptor," *Cytokine & Growth Factor Reviews*, 14:241-249 (2003).

Williamson et al., "IL-12 Is a Central Mediator of Acute Graft-Versus-Host Disease in Mice", *J. Immunol.*, pp. 689-699 (1996).

Winkles et al., "TWEAK and Fn14: New molecular targets for cancer therapy?" *Cancer Letters*, pp. 1-7 (2005).

Zhao et al., "Different Gene Expression Patterns in Invasive Lobular and Ductal Carcinomas of the Breast," *Mol. Biol. Cell*, 15:2523-2536 (Jun. 2004).

* cited by examiner

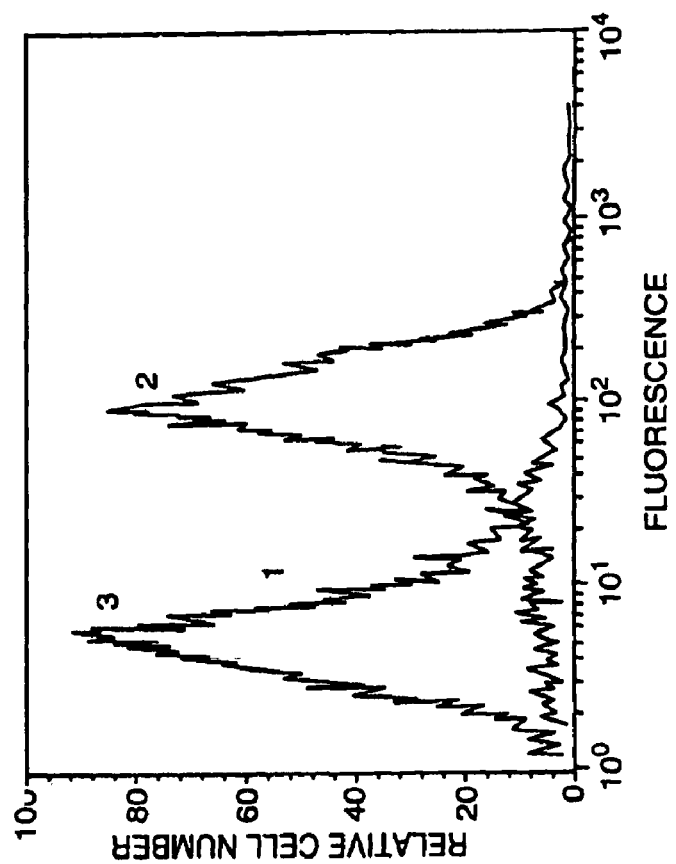
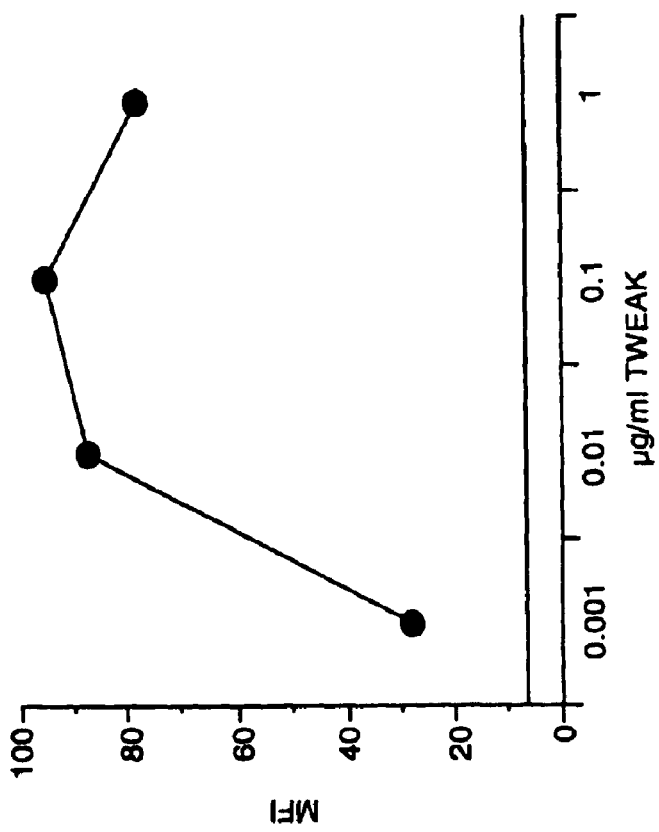
FIG. 1B
FIG. 1A

Untreated　　　　TWEAK

FIG. 10A

Type I Transmembrane Protein Fn14 (Homo sapiens)

```
  1 margsirril rllvlglwla llrsvageqa pgtapcsrgs swsadldkcm dcascrarph
 61 sdfclgcaaa ppapfrllwp ilggalsltf vlgllsgflv wrrcrrrekf ttpieetgge
121 gcpavaliq
```

FIG. 10B

Type I Transmembrane Protein Fn14 (Mus musculus)

```
  1 mapgwprslp qilvlgfglv lmraaageqa pgtspcssgs swsadldkcm dcascparph
 61 sdfclgcaaa ppahfrllwp ilggalslvl vlalvssflv wrrcrrrekf ttpieetgge
121 gcpgvaliq
```

TWEAK RECEPTOR AGONISTS AS ANTI-ANGIOGENIC AGENTS

CROSS REFERENCE TO RELATED APPLICATIONS

This application is a continuation application of U.S. application Ser. No. 10/380,611, filed Mar. 14, 2003, which issued on Apr. 24, 2007, as U.S. Pat. No. 7,208,151, which is a National Stage entry of PCT/US01/28451, filed Sep. 12, 2001, which claims priority to U.S. application Ser. No. 60/232,355, filed Sep. 14, 2000. The contents of each of the foregoing applications are incorporated in their entireties by reference herein.

BACKGROUND

Angiogenesis is an integral component of tissue remodeling during a variety of normal and pathological events, such as the female reproductive cycle, fetal development, wound healing, inflammation and tumor progression (Han, Z. C., and Y. Liu, *Int. J. Hematol,* 70(2):68 (1999); Folkman, J., *Nat. Med.,* 1(1):27 (1995)). The growth of microvessels involves the coordinated migration, proliferation, differentiation and morphogenetic organization of endothelial cells ("EC") into new capillary structures. Further stabilization and maturation of neovessels occurs through the recruitment of adjacent mesenchymal cells to the vessel walls (Bussolino, F. A., *Trands Biochem Sci.,* 22(7):251 (1997)). The maintenance of developing and quiescent vessels critically depends on the availability of appropriate survival signals. These angiogenic events are orchestrated by a network of extracellular factors, including several classes of cytokines, extracellular matrix and integrins, and by their cognate receptors.

A number of known angiogenic regulators belong to the Tumor Necrosis Factor (TNF) family. Ligands of this family are expressed as type II membrane proteins which may be proteolytically cleaved to produce soluble cytokines (Smith, C. A. et al., *Cell,* 76:959 (1994)). These ligands trigger biological activities by binding and signalling through their corresponding receptors in the TNF receptor family. The majority of the TNF family members mediate host defense, inflammation and immunological regulation (Vassalli, P., *Annu Rev Immunol,* 10:411 (1992); De Togni, P. J. et al., *Science,* 264(5159):703 (1994); Nagata, S., and Goldstein, P., *Science,* 267:1449 (1995); Foy, T. M. et al., *Annu Rev Immunol,* 14:591 (1996); Mackay, F. et al., *J Exp Med,* 190(11) 1697 (1999)). In addition, some of these ligands, including TNF-α, Fas ligand (FasL), Vascular Endothelial Growth Inhibitor (VEGI) or TL1, and TWEAK have been shown to regulate EC functions (Frater-Schroder, M. W. et al., *Proc. Natl. Acad. Sci. USA,* 84:5277 (1987); Yoshida, S. et al., *Mol Cell Biol,* 17(7):4015 (1997); Ruegg, C. et al., *Nat Med,* 4(4):408 (1998); Fajardo, L. F. et al., *Am J Pathol,* 140(3):539 (1992); Leibovich, S. J., *Nature,* 329(6140):630 (1987); Biancone, L., *J Exp Med,* 186(1):147 (1997); Yue, T. et al., *J. Biol. Chem.,* 274:1479 (1999); Zhai, Y., et al., *Faseb J,* 13(1): 181 (1999)). The effects of TNF-α on EC behavior are complex. TNF-α inhibits EC growth yet induces capillary tube formation in vitro (Frater-Schroder, M. et al., *Proc. Natl. Acad. Sci. USA,* 84:5277 (1987); Yoshida, S. et al., *Mol Cell Biol,* 17(7):4015 (1997)). It also can be antiangiogenic in the context of solid tumors (Ruegg, C. A., *Nat Med,* 4(4):408 (1998)) or angiogenic in corneal settings in vivo (Frater-Schroder, M. et al., *Proc. Natl. Acad. Sci. USA,* 84:5277 (1987); Yoshida, S. et al., *Mol Cell Biol,* 17(7):4015(1997); Fajardo, L. F. et al., *Am J Pathol,* 140(3):539 (1992); Leibovich, S. J. et al., *Nature,* 329(6140):630 (1987)). Fas/FasL interaction can induce endothelial capillary tube formation in vivo, probably by triggering the production of heparin-binding growth factors (Biancone, L. et al., *J Exp Med,* 186(1):147 (1997)), while VEGI inhibits EC survival and proliferation (Zhai, Y. et al., *Faseb J,* 13(1):181 (1999); Yue, T. et al., *J. Biol. Chem.,* 274:1479 (1999)). TWEAK, a novel member of the TNF ligand family (Chicheportiche, Y. et al., *J Biol Chem,* 272(51):32401 (1997)), induces the expression of the angiogenic chemokine Interleukin-8 (IL-8) in some epithelial tumor cell lines. Recently, TWEAK was reported to induce both proliferation of cultured human ECs under reduced growth factor conditions and corneal neovascularization (Lynch, C. N. et al., *J. Biol. Chem.,* 271(13):8455 (1999)).

Through the use of expression cloning, a receptor protein for TWEAK has recently been identified as "Fn14." This protein was originally characterized as an FGF-1 induced immediate early response gene (*J. Biol. Chem.* 274:33166-33176 (1999) and WO 98/55508). Fn14 has a more restricted expression pattern in adult tissues (as compared to TWEAK) and is the smallest TNF receptor described to date, with only one cysteine-rich repeat.

SUMMARY OF THE INVENTION

In addition to the roles played by TWEAK and Fn14 in inducing angiogenesis (see WO 01/45730), the present inventors have discovered that Fn14 agonists or activating agents (e.g., TWEAK and agonist anti-Fn14 monoclonal antibodies) actually (1) inhibit angiogenesis and (2) slow tumor progression, either indirectly through inhibition of angiogenesis or by direct anti-tumor activity.

Accordingly, the present invention provides methods of modulating angiogenesis by administering a therapeutically-effective amount of an agonist to a TWEAK receptor. In preferred embodiments, the TWEAK receptor is Fn14. In other preferred embodiments, the Fn14 receptor agonist is TWEAK or an anti-Fn14 monoclonal antibody. The present invention preferably provides methods of inhibiting angiogenesis by administering a therapeutically effective amount of an agonist to a TWEAK receptor.

The invention also includes methods of inhibiting tumor progression by administering a therapeutically-effective amount of an agonist to a TWEAK receptor. In preferred embodiments, the TWEAK receptor is Fn14. In other preferred embodiments, the Fn14 agonist is TWEAK or an anti-Fn14 monoclonal antibody.

The invention also contemplates pharmaceutical compositions comprising a therapeutically-effective amount of an agonist to a TWEAK receptor and a pharmaceutically-acceptable carrier.

To the extent that methods of the present invention contemplate modulating angiogenesis, they are useful as a treatment in diseases where enhanced angiogenic activity is desirable to promote neovascularization. Such diseases and conditions include: myocardial ischemic conditions (e.g., myocardinal infarction, improve blood flow in patents with coronary artery disease suffering from myocardial ischemia or inadequate blood flow to areas other than the heart such as in peripheral vascular disease, where decreased blood flow is a problem, revascularization of necrotic tissue, for example of the myocardium after an infarction or an angioplasty, angina, heart transplants, vascular grafts, and reopening vessels to improve vascularization, perfusion, collagenization and organization of said lesions), wound healing, and tissue and organ transplantations (e.g., enhancement of autologous or heterologous microvascular transplantation). Promotion of wound healing includes healing of incisions, bone repair, burn healing, post-infarction repair in myocardial injury, healing of gastric ulcers and other ulcers of the gastrointestinal tract and generally in promoting the formation, maintenance and repair of tissue. Neovascularization of grafted or transplated tissue is also contemplated, especially in subjects suffering from vascular insufficiency, such as diabetic patients.

To the extent that the methods of the present invention contemplate inhibiting angiogenesis, they are useful as treatment in diseases where diminished angiogenic activity is desirable to inhibit neovascularization. Such conditions include cancer, inflammatory macular degeneration, and diabetic retinopathy.

To the extent that the methods of the present invention contemplate inhibiting tumor progression, they are useful to treat conditions associated with undesired cell proliferation, such as cancers, including but not limited to, prostate cancers, lymphomas, adenocarcinomas, neuronal neoplasms, colon cancers, pancreatic tumors, paraganglioma, breast cancer, renal cell cancers, lung cancers, ovarian cancers, leiomyomas, lung cancers, memingiomas, pheochromacytomas, osteosarcomas and thyroid cancers.

BRIEF DESCRIPTION OF THE DRAWINGS

FIG. 1A and FIG. 1B depict two plots in which Mean Fluorescence Intensity (MFI) vs. TWEAK concentration is shown (left), with the dotted line indicating the background MFI with the indirect detection step alone. Histograms (right) correspond to (1) background fluorescence with indirect detection step alone, (2) TWEAK binding, and (3) inhibition of TWEAK binding by the AB.D3 mAb.

FIG. 9A-1, FIG. 9A-2, FIG. 9B-1 and FIG. 9B-2 depict growth of Lewis Lung Carcinoma in TWEAK-transgenic mice plotted as tumor weight (mg) at days post implantation.

FIG. 10A. Amino acid sequence (SEQ ID NO:1) of Type I transmembrane protein Fn14 [*Homo Sapiens*].

FIG. 10B. Amino acid sequence (SEQ ID NO:2) of Type I transmembrane protein Fn14 [*Mus Musculus*].

DETAILED DESCRIPTION OF THE INVENTION

Figure 2B:
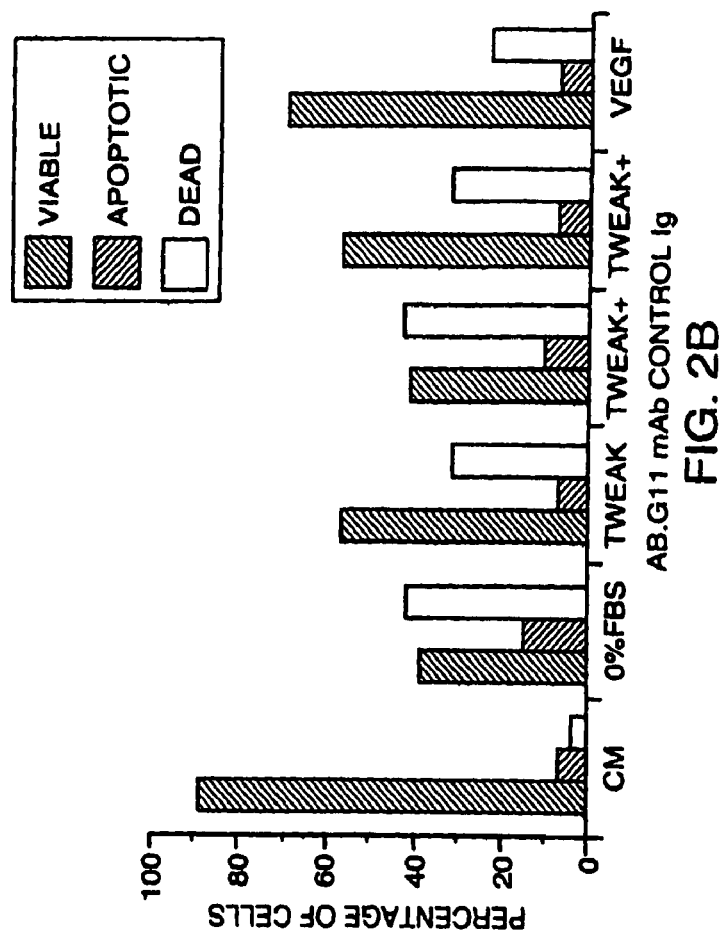
FIG. 2 depicts two bar graphs showing percentage of (A) HUVEC and (B) HDMEC cells that were viable apoptotic or dead after treatment with TWEAK. EC were cultured for 48 hours in CM (CS-C Complete Media containing 10% FBS and growth supplements), 0% FBS (CS-C media without FBS and growth supplements and supplemented with 0.1% BSA and 10 µg/ml heparin), and 0% FBS with TWEAK or VEGF. Anti-TWEAK mAb AB.G11 and control Ig were added as specified. Cells were stained with FITC-Annexin-V and PI and the percentage of viable, apoptotic and dead cells indicated. Each of these results is representative of two independent experiments.

In order that the invention herein described may be fully understood, the following detailed description is set forth.

The term "anti-tumor activity" refers to the ability of a substance or composition to block the proliferation of, or to induce the death of tumor cells which interact with that substance or composition.

The term "inhibition of tumor progression" refers to the ability of a substance or compound to block the proliferation of, or to decrease growth and development of tumor cells which interact with that substance or compound.

The term "apoptosis" refers to a process of programmed cell death.

The term "cytotoxic activity" refers to the ability of a substance or composition to induce the death of cells which interact with that substance or composition.

The term "epitope" (or antigenic determinant) is defined as the part of a molecule that combines with a single antigen binding site on an antibody molecule. A single epitope is recognized by a monoclonal antibody (mAb). Multiple epitopes are normally recognized by polyclonal antibodies (Ab).

The term "angiogenic factor" refers to factors which promote the angiogenic process, including but not limited to the following phases of the process, ie, the degradation of the extracellular matrix, cell proliferation, cell migration and structural organization (Kumar et al., *Int. J. Oncology* 12:749-757 (1998); Bussolino et al., *Trends in Biochem,* 22:251-256 (1997)). Angiogenic factors include but are not limited to fibroblast growth factor (bFGF), acidic FGF (aFGF), FGF-5, vascular endothelial growth factor isoforms (VEGF), angiopoietin-1 (Ang-1) and angiopoietin-2 (Ang-2), Platelet-derived endothelial cell growth factor (PD- ECGF), hepatocyte growth factor, proliferin, B61, soluble vascular cell adhesion molecular-1, soluble E-selection, 12-hydrozyeicosatetraenoic acid, Tat protein of HIV-1, angiogenin, TNF α, FasL, Transforming growth factor-β.

The "Fc domain" of an antibody refers to a part of the molecule comprising the CH2, CH3 and hinge regions but lacking the antigen binding sites.

The term "Fn14" refers to the TWEAK receptor protein as characterized in *J. Biol. Chem.* 274:33166-33176 (1999), the entire disclosure of which is incorporated herein by reference. The human and mouse amino acid sequences for this type I transmembrane protein are provided in FIGS. 10A (SEQ ID NO:1) and 10B (SEQ ID NO:2).

The terms "Fn14 agonist" or "Fn14 activating agent" refers to any agent which can augment ligand binding to Fn14, Fn14 signaling, or which can influence how the Fn14 signal is interpreted within the cell. Examples of Fn14 agonists include TWEAK, soluble anti-Fn14 Abs, cross-linked anti-Fn14 Abs and multivalent anti-Fn14 Abs.

The term "Fn14 signaling" refers to all molecular reactions associated with the Fn14 pathway and subsequent molecular reactions which result therefrom.

The term "anti-Fn14 antibody" ("anti-Fn14 Ab") refers to any antibody that recognizes and binds to at least one epitope of the Fn14 receptor.

The term "anti-Fn14 monoclonal antibody" ("anti-Fn14 mAb") refers to any monoclonal antibody that recognizes and binds to a single epitope of the Fn14.

The term "cross-linked anti-Fn14 (m)Abs" refer to antibodies directed against the Fn14 which have either been cross-linked to each other to form antibody agglomerates in solution using an anti-Fn14 antibody (Ab) or (mAb) cross-linking agent, or which have been immobilized in close proximity to one another on a surface or matrix.

The term "anti-Fn14 Ab (or mAb) cross-linking agent" refers to any agent which can covalently or non-covalently aggregate anti-Fn14 Abs in solution so that the Abs can bind to and potentiate target cell surface Fn14 clustering. Such cross-linking agents include but are not limited to chemical cross-linking agents, secondary antibodies which react with portions of the anti-Fn14 Abs or mAbs, and soluble or surface-bound Fc receptors—either endogenous or added exogenously—which can bind to anti-Fn14 Abs.

The term "multivalent ligand" refers to a molecule or complex which has more than one receptor binding site and which is capable of simultaneously binding and bringing into close proximity at least two receptor molecules.

A "type I leader sequence" is an amino-terminal portion of a eukaryotic protein which serves as a signal to direct the protein to the endoplasmic reticular (ER) membrane and often through the entire secretion pathway. The leader sequence is usually cleaved off by a signal peptidase in the ER membrane.

A "signal sequence" is the functional equivalent of a eukaryotic type I leader sequence in prokaryotic hosts, and directs the translocation of proteins into or across lipid bilayer membranes of a bacterium.

Source of Anti-Fn14 Antibodies

Anti-protein (anti-peptide antisera or monoclonal antibodies can be made by standard protocols (see, for example, *Antibodies: A Laboratory Manual*, ed. by Harlow and Lane, Cold Spring Harbor press: 1988).

Polyclonal antibody sera directed against the human Fn14 are prepared using conventional techniques by injecting animals such as goats, rabbits or mice subcutaneously with a human Fn14 Fc fusion protein in complete Freund's adjuvant, followed by booster intraperitoneal or subcutaneous injection in complete Freunds. Polyclonal antisera containing the desired antibodies which are directed against Fn14 are screened by conventional procedures.

Mouse monoclonal antibodies (mAbs) directed against a human Fn14 Fc fusion protein are prepared by intraperitoneal immunization of RBF mice repetitively with a CHO cell-derived recombinant Fn14 Fc fusion protein (Fn14 Fc) attached to protein A sepharose beads in the absence of adjuvant. Animals are finally boosted with soluble Fn14 Fc (both i.p. and i.v.), spleen cells are fused using classical protocols, and hybridomas are screened by ELISA (Ling et al., J. Interferon and Cytokine Res., 15, pp. 53-59 (1995)). Pure mAbs are prepared by protein A sepharose purification of IgG from hybridoma culture supernatants.

Various forms of anti-Fn14 antibodies can also be made using standard recombinant DNA techniques (Winter and Milstein, Nature, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., Proc. Natl. Acad. Sci. U.S.A., 81, pp. 6851-55 (1984)). Chimeric antibodies reduce the observed immunogenic responses elicited by animal antibodies when used in human clinical treatments.

In addition, recombinant "humanized antibodies" which recognize Fn14 can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject. Also, primatized and/or fully human mAbs can be generated using techniques well-known in the art, and can be utilized in the present invention.

Construction of different classes of recombinant anti-Fn14 antibodies can also be accomplished by making chimeric or humanized antibodies comprising the anti-Fn14 variable domains and human constant domains (CH1, CH2, CH3) isolated from different classes of immunoglobulins. For example, anti-Fn14 IgM antibodies with increased antigen binding site valencies can be recombinantly produced by cloning the antigen binding site into vectors carrying the human μ chain constant regions (Arulanandam et al., J. Exp. Med., 177, pp. 1439-50 (1993); Lane et al., Eur. J. Immunol., 22, pp. 2573-78 (1993); Traunecker et al., Nature, 339, pp. 68-70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling (Queen et al., Proc. Natl. Acad. Sci. U.S.A., 86, pp. 10029-33 (1989); WO 94/04679).

It may be desirable to increase or to decrease the affinity of anti-Fn14 Abs for Fn14 depending on the targeted tissue type or the particular treatment schedule envisioned. For example, it may be advantageous to treat a patient with constant levels of anti-Fn14 Abs with reduced ability to signal through the Fn14 pathway for semi-prophylactic treatments. Likewise, anti-Fn14 Abs with increased affinity for the Fn14 may be advantageous for short-term, tumor-targeted treatments.

Multiple Anti-Fn14 Abs in Solution Act as Fn14 Agonists

Compositions comprising multiple anti-Fn14 Abs in solution which act as Fn14 agonists are provided in this invention. Polyclonal anti-Fn14 Abs directed against different epitopes of the Fn14 can be used. Preferably, the anti-Fn14 Abs are monoclonal Abs directed against different and non-overlapping epitopes of the Fn14.

The combined anti-Fn14 mAb approach to Fn14 activation requires combining two non-overlapping epitopes. Additional epitopes (as defined by new mAbs) may be identified by continuing to fuse immunized mouse spleen cells, by immunizing different species of animals, and by using different routes of immunization.

Epitopes can also be directly mapped by assessing the ability of different mAbs to compete with each other for binding to the Fn14 using BIAcore chromatographic techniques (Pharmacia BIAtechnology Handbook, "Epitope Mapping", Section 6.3.2, (May 1994); see also Johne et al., J. Immunol. Methods, 160, pp. 20 191-8 (1993)).

Anti-Fn14 IgM Monoclonal Antibodies Function as Fn14 Agonist

Anti-Fn14 mAbs which comprise more than the usual two IgG antigen binding sites will also function in solution as cell surface Fn14 cross-linking agents, and will accordingly fall within the definition of a Fn14 agonist according to this invention. The antigen binding sites of an anti-Fn14 mAb can be built into IgM molecules—which have ten antigen binding sites—using standard recombinant DNA and hybridoma techniques.

Alternatively, one may collect and enrich for complete mouse (or other animal) IgM molecules isolated by hybridoma fusion techniques after a single immunization with antigen. One way to enrich for IgM molecules would be to immunize CD40 signaling-deficient mice (Kawabe et al., Immunity, 1, pp. 167-78 (1994); Xu et al., Immunity, 1, pp. 423-31 (1994)). These mice cannot effectively produce IgGs and therefore their response to challenge by antigen is enriched for IgM isotypes.

Anti-Fn14 IgM antibodies, by virtue of their increased valency, can effectively aggregate Fn14 molecules within the plane of the membrane, thereby enhancing Fn14 signaling as compared to their IgG counterparts having two antigen binding sites. A dramatic example of the increased efficiency of multivalent antibodies in receptor clustering is seen with antibodies to the Fas receptor, where the IgM form is very potent and normal bivalent IgGs are not effective in solution (Yonihara and Yonihara, J. Exp. Med., 169, pp. 1747-56 (1989); Alderson et al., Int. Immunol., 6, pp. 1799-1806 (1994)).

Likewise, the apo-1 mAb to the Fas receptor is an IgG3 mAb. This mAb is a potent cytotoxic agent which relies on Fc interactions unique to IgG3 subtypes to aggregate into larger polyvalent forms. Removal of the Fc region creates a F(ab)$_2$ form that cannot associate into larger aggregates and which is inactive (Dhein et al., J. Immunol., 149, pp. 3166-73 (1992)). Thus by analogy, it is predicted that IgM versions of anti-Fn14 mAbs will be potent anti-tumor agents.

Treatments Using Fn14 Agonist

The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment.

The therapeutic agents of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and intracapsular. Treatments are also preferably conducted over an extended period on an outpatient basis. Daily dosages of the therapeutic agents are expected to be in the range of about 0.01-1000 µg/kg body weight, and more preferably about 10-300 µg/kg body weight, although precise dosages will vary depending upon the particular therapeutic agent employed and the particular subject's medical condition and history.

Administration of the anti-Fn14 Abs of this invention, including isolated and purified forms of the antibodies or complexes, their salts or pharmaceutically acceptable derivatives thereof, may be accomplished using any of the conventionally accepted modes of administration of agents which exhibit anti-tumor activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The anti-Fn14 Abs may, for example, be placed into sterile, isotonic formulations with or without cofactors which stimulate uptake or stability. The formulation is preferably liquid, or may be lyophilized powder. For example, the anti-Fn14 Abs may be diluted with a formulation beffer comprising 5.0 mg/ml citric acid monohydrate, 2.7 mg/ml trisodium citrate, 41 mg/ml mannitol, 1 mg/ml glycine and 1 mg/ml polysorbate 20. This solution can by lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16$^{th}$ Editin, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeably polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and gamma ethyl-L-glutamate (Sidman et al., Biopolymers, 22, pp. 547-56 (1985)); poly(2-hydroxyethyl-methacrylate) or ethylene vinyl acetate (Langer et al., J. Biomed. Mater. Res., 15, pp. 167-277 (1981); Langer, Chem. Tech., 12, pp. 98-105 (1982)).

Liposomes containing anti-Fn14 Abs can be prepared by well-known methods (See, e.g. DE 3,218,121; Epstein et al., Proc. Natl. Acad. Sci. U.S.A., 82, pp. 3688-92 (1985); Hwang et al., Proc. Natl. Acad. Sci. U.S.A., 77, pp. 4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of anti-Fn14 Abs release.

The anti-Fn14 Abs of this invention may also be attached to liposomes containing other Fn14 activating agents, chemotherapeutic agents to supplement the IFN-γ typically found in the region of tumors. Attachment of TWEAK complexes and anti-Fn14 Abs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

It is envisioned that the mAbs would be administered to tumor-bearing people in conjunction with a conventional anti-tumor therapy (i.e. radiation and chemotherapy). A combined treatment of Fn14 activation with conventional chemotherapies may provide an extra factor of tumor killing activity that would be more likely to clear a patient of tumorigenic cells than when conventional anti-tumor therapy is used alone.

It is further possible that this approach may have relatively few side effects and therefore could be given in a semi-prophylactic sense in cases of carcinomas that may not have metastasized, or in patients from families who show a genetic pre-disposition for a certain type of cancer.

The following are examples which illustrate the methods of this invention. These examples should not be construed as limiting: the examples are included for purposes of illustration and the present invention is limited only by the claims.

EXAMPLES

Example 1

TWEAK Modulates Endothelial Cell Responses to Basic Fibroblast Growth Factor and Vascular Endothelial Growth Factor Cells and Culture Conditions—Human Umbilical Vein Endothelial Cells (HUVEC) and Human Dermal Microvascular Endothelial Cells (HDMEC) were obtained from Cell System Corporation (CS-C) (Kirkland, Wash.) or Clonetics (San Diego, Calif.). Aortic EC, aortic smooth muscle cells, lung fibroblasts, embryonic myoblasts and human peripheral blood dendritic cells were purchased from Clonetics. HUVEC and HDMEC were routinely passaged in CS-C Complete Medium which contains 10% fetal bovine serum (FBS) and supplier growth supplement and were used in experiments until passage seven. Survival studies were performed in CS-C Complete Media and CS-C Media (without FBS and without growth supplement) as specified. For the proliferation, migration and immunofluorescent staining experiments, EC Basal Medium (EBM) containing 2% FBS and supplier growth supplements, defined herein as "complete media" and EBM containing 2% FBS, defined herein as "basal media", were used (Clonetics). For the capillary tube formation assay, EC Basal Medium 2 (EBM-2) with 5% FBS and supplier growth supplements were used (Clonetics). The MS-1 and M210B4 cell lines were purchased from American Type Culture Collection (Manassas, Va.). Mouse lymphoid cells were obtained 24 to 48 hours after in vivo activation with 200 μg/ml of anti-CD3 monoclonal antibody (mAb) (clone 2C11) (Pharmingen, San Diego, Calif.). Thioglycollate-induced peritoneal macrophages were stimulated in vitro for 48 hours with interferon gamma (IFNγ) (100 Units/ml), TNF-α (10 ug/ml) or Lipopolysaccharide (LPS) (1 ug/ml).

Reagents and Antibodies—Recombinant human bFGF was obtained as a growth supplier supplement (Clonetics), and bFGF and VEGF also were purchased from R&D Systems (Minneapolis, Minn.) and Sigma (St. Louis, Mo.). Annexin V-FITC and propidium iodide (PI) were from Pharmingen. Mouse anti-human TNF-α and mouse anti-human IL-8 mAbs from R&D (Minneapolis, Minn.) and isotype-matched control Ig MOPC21 (ICN Biomedicals Inc., Irvine, Calif.) were used for blocking studies. Biotin-conjugated anti-FLAG from Eastman Kodak Company (New Haven, Conn.), and Phycoerythrin (PE)-Streptavidin from Southern Biotechnology Associates, Inc. (Birmingham, Ala.).

TWEAK-specific mAbs—BE.B3, AB.G11 and AB.D3 were generated in Armenian hamsters by immunizing with soluble human TWEAK protein and standard hybridoma generation procedures. The ability of AB.D3 and AB.G11 to bind to human and murine TWEAK and BE.B3 to bind to human TWEAK was demonstrated in an ELISA assay using recombinant soluble TWEAK proteins immobilized on 96 well microtiter plates. The blocking activity of AB.D3 and AB.G11 were demonstrated by these mAbs but not BE.B3 to inhibit soluble flag-tagged human TWEAK binding to HT29 cells in a FACS analysis. BE.B3 was biotinylated using ImmunoPure Biotinylation kits following the manufacturer's protocol (Pierce, Rockford, Ill.). A hamster control Ig (clone Ha4/8-3.1) was obtained from the American Type Culture Collection and mAb was purified from culture supernatant by Protein A Fast Flow column (Pharmacia, Piscataway, N.J.).

Recombinant Soluble Human TWEAK protein—Recombinant soluble human TWEAK (GenBank Accession #AF030099) containing amino acid residues A106-H249 was expressed either with or without an N-terminal flag epitope in the yeast *Pichia pastoris* (Invitrogen, location). The fermentation medium from *pichia* expressing soluble human TWEAK was concentrated and dia-filtrated in 20 mM Tris-HCl, pH 8.0 and ion-exchanged on a Q Sepharose column prior to loading onto a Zn-chelating column. The soluble TWEAK was eluted by an imidazole gradient in 20 mM sodium phosphate, 0.5 M sodium chloride, pH 7.5 prior to final fractionation by a size-excluded using a Sephacryl 300 column.

Analysis of Apoptosis—For serum starvation experiments, HUVEC or HDMEC were seeded in 6-well plates at a density of $1.2\times10^5$ cells per well and were incubated overnight in CS-C Complete Medium. Immediately before each experiment, cells were washed with phosphate-buffered saline (PBS) and cultured for 48 hours in CS-C Complete Media, or CS-C Media supplemented with 0.1% bovine serum albumin (BSA) and heparin (10 ug/ml), with or without VEGF (10 ng/ml) or TWEAK (200 ng/ml). Where indicated, 2 ug/ml of anti-TWEAK mAb AB.G11 or control Ig also were added. After 48 hours, cells were washed with PBS and detached by incubation with dispase (CS-C) for 15 minutes at 37° C. followed by replacement with PBS containing 5 mM EDTA and 0.1% BSA for 15 minutes at 37° C. After an additional wash in PBS, cells were stained with FITC-Annexin-V and 5 ug/ml PI according to the supplier. Fluorescence was analyzed within the hour using FACStar$^{PLUS}$ (Becton Dickinson, San Jose, Calif.).

Proliferation Assays—HUVEC were plated in 96-well microtiter plates at subconfluence (4000 cells per well) and cultured overnight in CS-C Medium without addition of supplier growth supplements. Media was replaced with complete media or with basal media as defined above. Cells were cultured in basal media with or without TWEAK (100 ng/ml), bFGF using a 1/500-1/1000 dilution of the bFGF supplement (Clonetics) or 1 ng/ml (R&D Systems), VEGF (10 ng/ml) or combinations of these factors. Where indicated, 10 ug/ml anti-TWEAK mAbs AB.D3, BE.B3 or hamster control Ig Ha4/8 also were added. Cells were incubated at 37° C. with 5% $CO_2$ for three days and proliferation was measured by pulsing with $^3$H-Thymidine for the last 10 hours of culture. Cell-bound radioactivity was measured with a Betaplate™ (EG&G Wallac, Gaithersburg, Md.).

Endothelial Wound Repair Assay—A standard wound repair assay was employed as previously described (Morales, D. E. et al., Circulation, 91(3):755 (1995)). In brief, a confluent monolayer of HUVEC was grown in CS-C Complete Medium in 35×10 mm cell culture dishes with 2 mm grids (Nalge Nunc International, Naperville, Ill.). The monolayer was wounded by two perpendicular strokes across the diameter of the dish with a 1 mm tip. Dislodged cells were aspirated and plates were rinsed with PBS. Cells were cultured for 18 hours in complete media or in basal media as defined above with or without TWEAK (200 ng/ml), bFGF (1/1000 or 1 ng/ml), VEGF (10 ng/ml) or combinations of these before fixing with 1% paraformaldehyde followed by staining with Harris Hematoxylin (Sigma, St. Louis, Mo.). Wound repair was quantified by visually counting the number of grids in which the gap was obscured by migrating cells. This number was divided by the total number of grids that aligned the wound and results were expressed as mean percentage wound repair +/−SEM.

Immunofluorescent staining—Cells were analyzed for TWEAK binding by incubation with flag-TWEAK and binding was detected with either biotinylated mouse anti-flag mAb or biotinylated BE.B3 and streptavidin-PE. Cold competition was performed with flag-TWEAK at 100 ng/ml and increasing concentrations of nontagged TWEAK, with binding detected with biotinylated mouse anti-flag mAb. Blocking of TWEAK binding by the AB.D3 Ab was performed by preincubation of flag-TWEAK with 10 μg/ml of mAb.

Capillary tube formation assay—Capillary tube formation by ECs was analyzed using a fibrin matrix gel assay based on a method previously described (Mach et al., Am J Pathol 154, (1):229 (1999)). Briefly, 4 mg/ml plasminogen free human fibrinogen (Calbiochem, San Diego, Calif.) was dissolved in serum free EBM-2 media with heparin and polymixin B both at 1 ug/ml (Sigma) as well as all of the supplier supplements except for VEGF and bFGF. The fibrin solution was filtered-sterilized and fibrin matrices were prepared by adding thrombin (20-50 milliunits/ml) (Sigma) and distributing 300 ul per well in 24-well plates. HUVEC ($4×10^4$ cells/$cm^2$) were seeded onto the gel surfaces and overlayered with EBM-2 media as above and 5% FBS in the presence or absence of TWEAK, bFGF, VEGF or combinations of these factors. TWEAK was used at 1 ug/ml or 100 ng/ml with similar results obtained, bFGF at 100 ng/ml, and VEGF at 50 ng/ml. In some experiments, neutralizing mAbs specific for TNF (1 ug/ml) and IL-8 (10 ug/ml) or isotype control Ig were used. After 48-72 hours of culture, phase-contrast photomicrographs of the gel surface were taken. Gels were fixed with 10% ethanol for 10 minutes, transferred from the original wells to new wells, fixed with 4% paraformaldehyde, embedded in paraffin, cross sectioned (5 microns) and stained with Hematoxylin and eosin.

RNAse Protection Assay (RPA)—RPA was performed using the hAngio multiprobe Template Set (Pharmingen). HUVEC were cultured as adherant monolayers in EBM-2 media with 5% FBS and supplier supplements except for bFGF and VEGF. TWEAK, VEGF or VEGF+TWEAK were added and RNA was isolated after 16 hours of culture.

Figures 1, 9A:
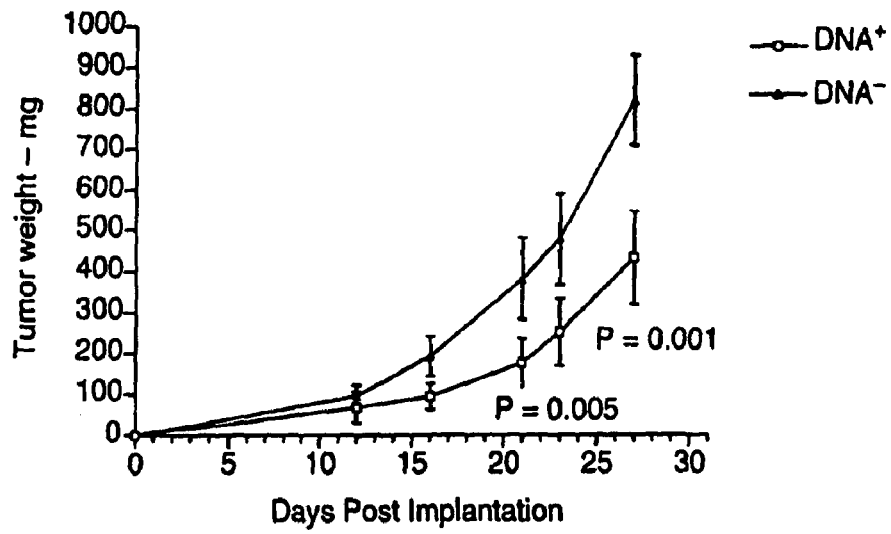
Figures 2, 9A:
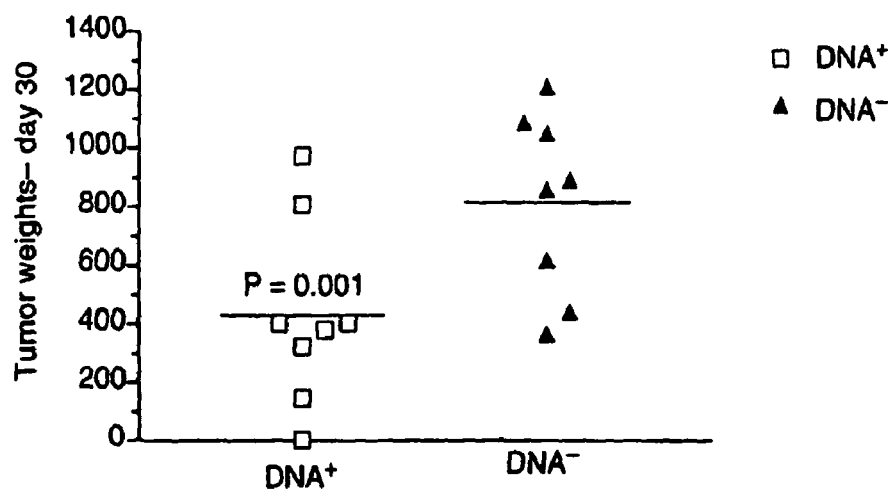
Figures 1, 9B:
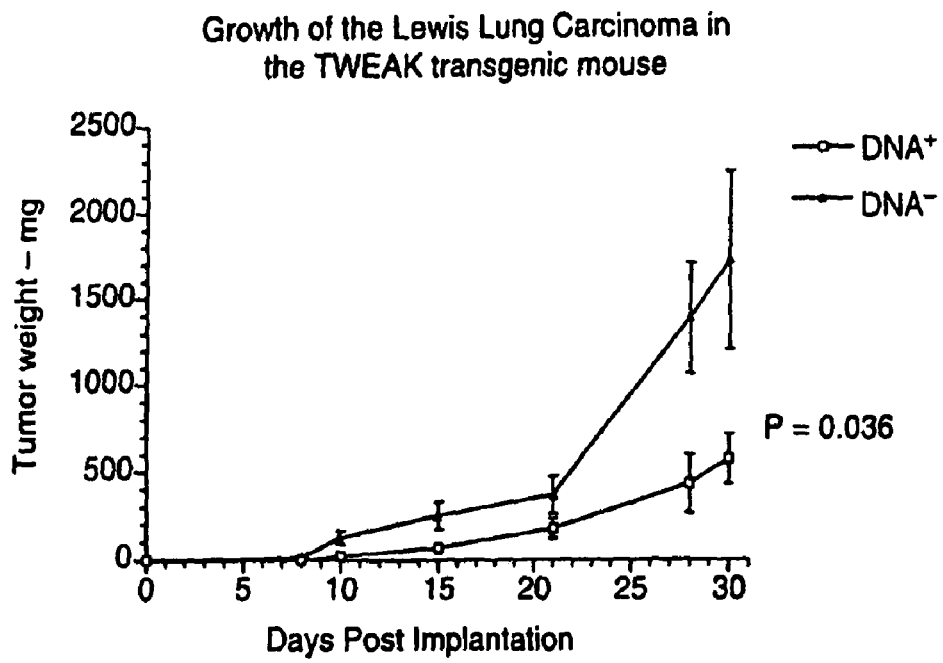
Figures 2, 9B:
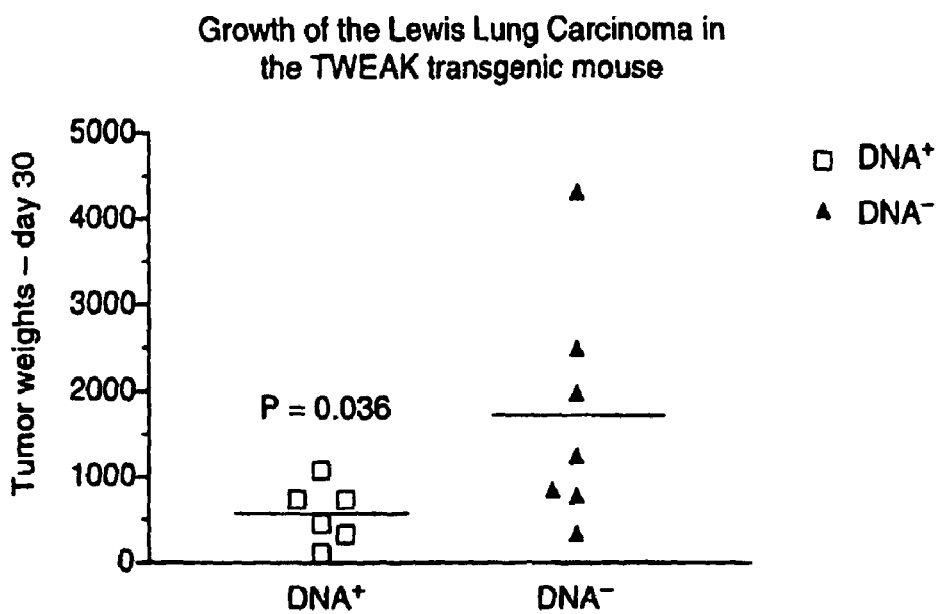

Results:

TWEAK binding is cell type-restricted—In order to determine which cell types might be targets for TWEAK activity, we surveyed various primary cells for their ability to bind to recombinant soluble human TWEAK by immunofluorescent staining. As shown in Table I, TWEAK bound to human venous and aortic ECs, aortic smooth muscle cells, embryonic myoblasts and to a lower degree to lung fibroblasts. Flag-TWEAK binding was dose-dependent and specific as evidenced by blocking with the AB.D3 mAb and by cold competition with an independent TWEAK preparation (FIG. 1 and data not shown). Similarly, TWEAK bound to murine EC and fibroblast cell lines. However, TWEAK did not bind detectably to any human leukocytes, either freshly isolated or activated under a variety of conditions.

Figure 2A:
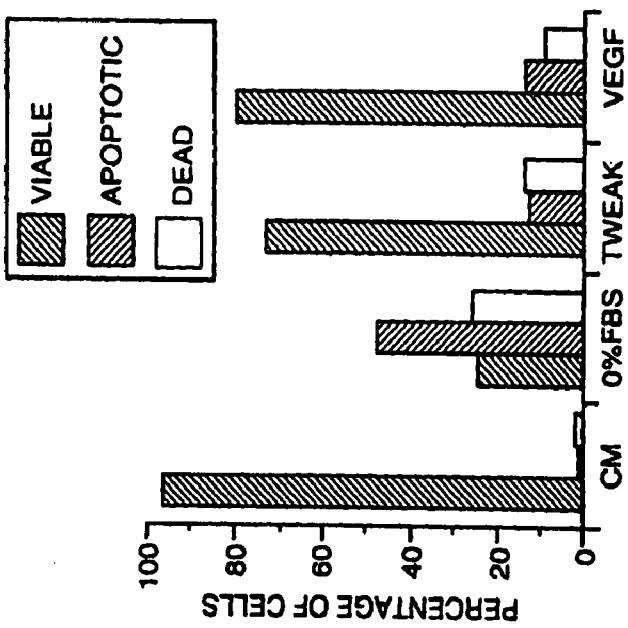

TWEAK promotes EC survival—The ability of TWEAK to promote EC survival was tested by culturing HUVEC in serum-free media in the absence or presence of TWEAK. HUVEC viability under these conditions was compared with that in serum-free media supplemented with VEGF (Nor, J. E. et al., Am J Pathol, 154(2):375 (1999)) or in CS-C Complete Media. Cell viability was measured by standard double staining with Annexin-V, an early marker for apoptosis, and PI dye exclusion. As shown in FIG. 2A, cells cultured in CS-C Complete Media remained viable at 48 hours (97%), whereas in serum-free cultures without additional factors the viable cells decreased to 25% and a significant fraction of apoptotic (48%) and dead cells (26%) appeared. However, in the presence of TWEAK, HUVECs remained largely protected from apoptosis (73% viable). The degree of EC survival achieved with TWEAK was comparable to that with VEGF. The survival of HDMEC in serum-free media also was enhanced by TWEAK but to a lesser degree than HUVECs, and this activity was specifically inhibited by anti-TWEAK mAb AB.G11 (FIG. 2B).

Figure 3B:
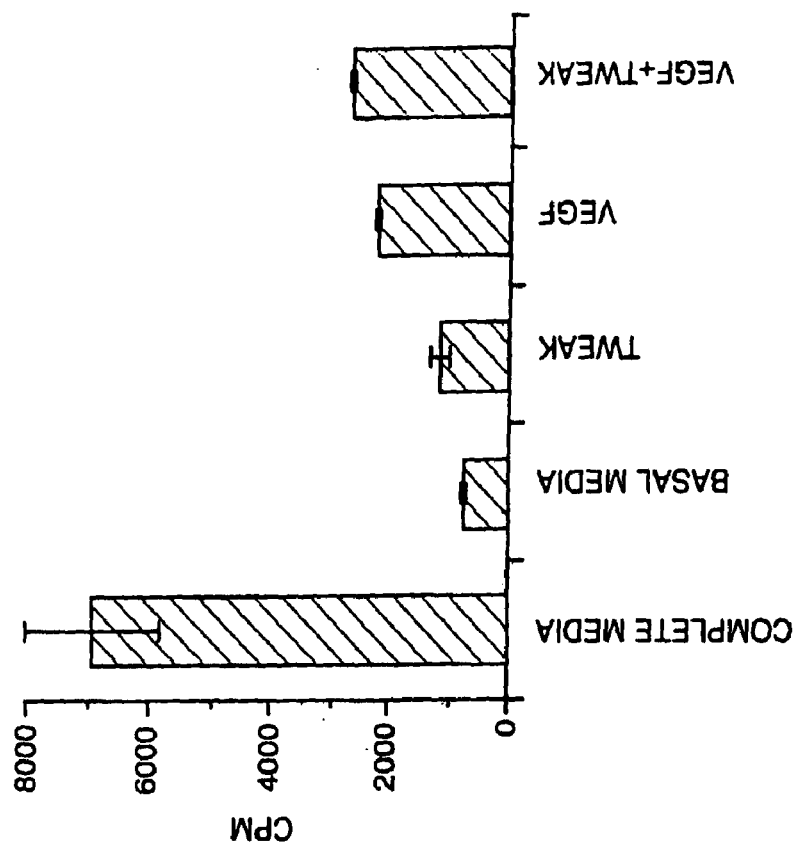
FIG. 3 depicts two bar graphs showing bFGF-dependent proliferation. HUVEC were cultured for 3 days in complete media or in basal media. TWEAK (100 ng/ml), bFGF (1/500 dilution) VEGF (10 ng/ml) or combinations of these factors were added to basal media as indicated and proliferation measured by $^3$H-thymidine incorporation. (A) Data shown are the mean value +/−SD of triplicate wells. These results are representative of 4 independent experiments. In addition to growth factors, blocking anti-TWEAK mAb AB.D3, non-blocking anti-TWEAK mAb BE.B3, and an irrelevant hamster control Ig Ha4/8 (10 ug/ml) were added where indicated, with results representative of two independent experiments. (B) Results shown are the mean value +/−SD of triplicate wells and are representative of 4 independent experiments.
Figure 3A:
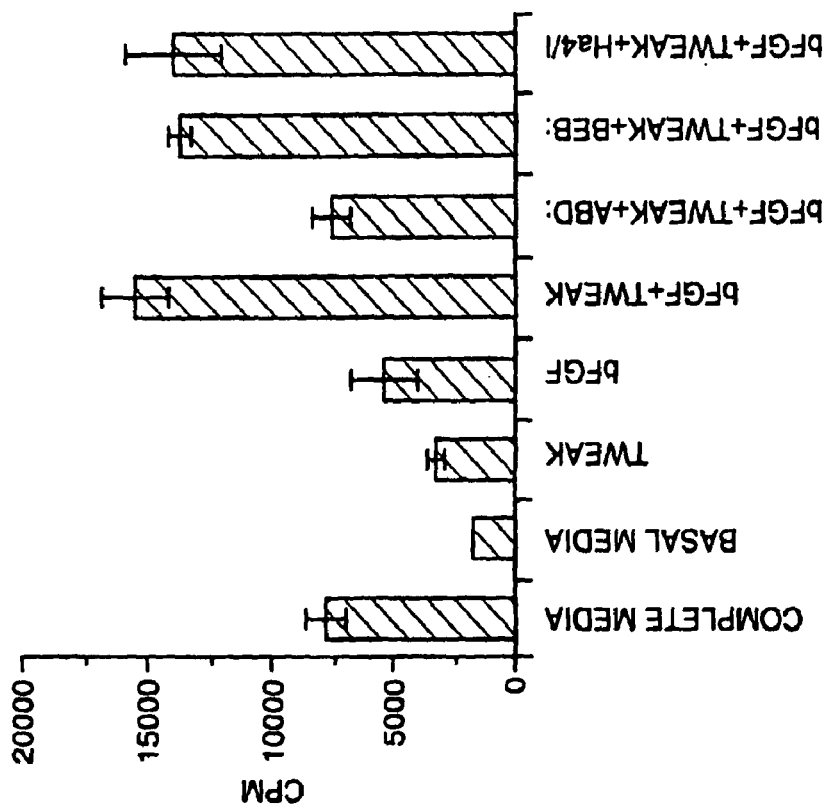

TWEAK cooperates with bFGF to increase EC proliferation—We further examined the effect of TWEAK on proliferation by measuring $^3$H-thymidine incorporation of HUVEC cultured in basal media with TWEAK, alone or in combination with two key angiogenic factors. TWEAK induced a small but not significant increase in HUVEC proliferation, on average a 1.6 fold increase relative to basal medium (n=7 independent experiments). By contrast, the cells cultured with TWEAK and bFGF displayed a significantly enhanced proliferative response as compared to cells cultured in the presence of bFGF alone (FIG. 3A). The level of $^3$H-thymidine incorporation achieved was comparable to or greater than that of ECs cultured in complete media. Similar results were obtained using bFGF at 1 ng/ml. The synergistic activity of TWEAK with bFGF was completely inhibited by anti-TWEAK mAb AB.D3 indicating that the effect of TWEAK was specific, whereas there was no inhibition by a anti- TWEAK mAb BE.B3 or a control Ig. By contrast, TWEAK did not affect the proliferative response to VEGF (FIG. 3B).

Figure 4:
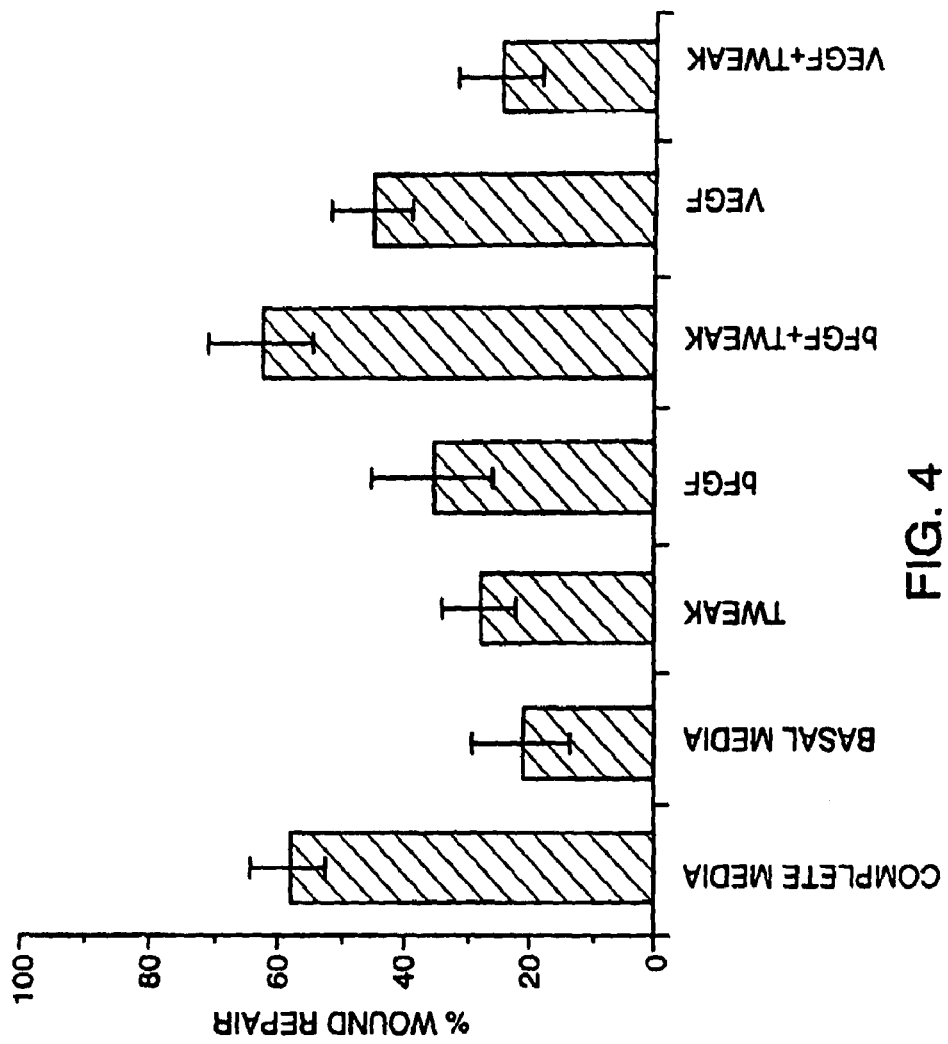
FIG. 4 depicts a bar graph showing the effect of TWEAK on bFGF-dependent HUVEC migration. Confluent HUVEC monolayers treated with TWEAK, bFGF, VEGF, and combinations of these factors were wounded and repair measured after 18 hours of culture. Results shown are the average of 4 experiments +/−SEM.

TWEAK enhances bFGF-dependent and inhibits VEGF-dependent EC migration—The ability of TWEAK to effect EC migration also was evaluated in the presence and absence of other angiogenic factors. Confluent HUVEC monolayers were wounded and EC migration was monitored within the first 18 hours by determining the degree of wound repair. Addition of TWEAK or bFGF to the basal media induced a low level of wound repair. By contrast, cultures treated with both TWEAK and bFGF were repaired more efficiently than cultures kept in basal media or stimulated with either agent alone (FIG. 4). By contrast, wound repair was decreased in cultures treated with TWEAK+VEGF as compared to those with VEGF alone. Thus TWEAK cooperates with bFGF and antagonizes the effect of VEGF on wound repair.

Figure 5A:
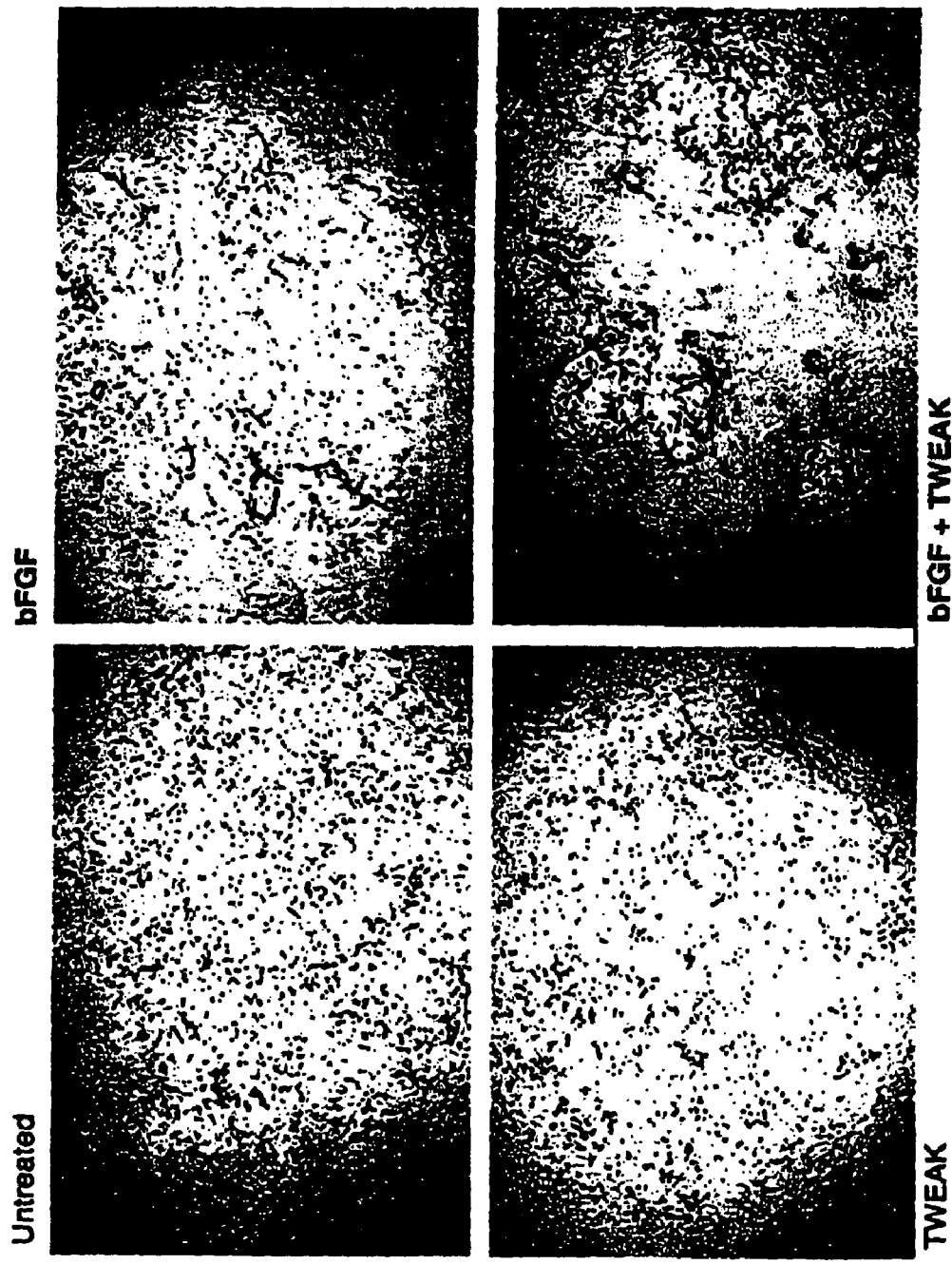
FIG. 5(A) depicts phase contrast images of HUVECs on the surface of fibrin gel matrices after 3 days of culture, untreated or treated with bFGF, TWEAK or bFGF+TWEAK. All images are 4× magnification. These results are representative of 8 independent experiments.
Figure 5B:
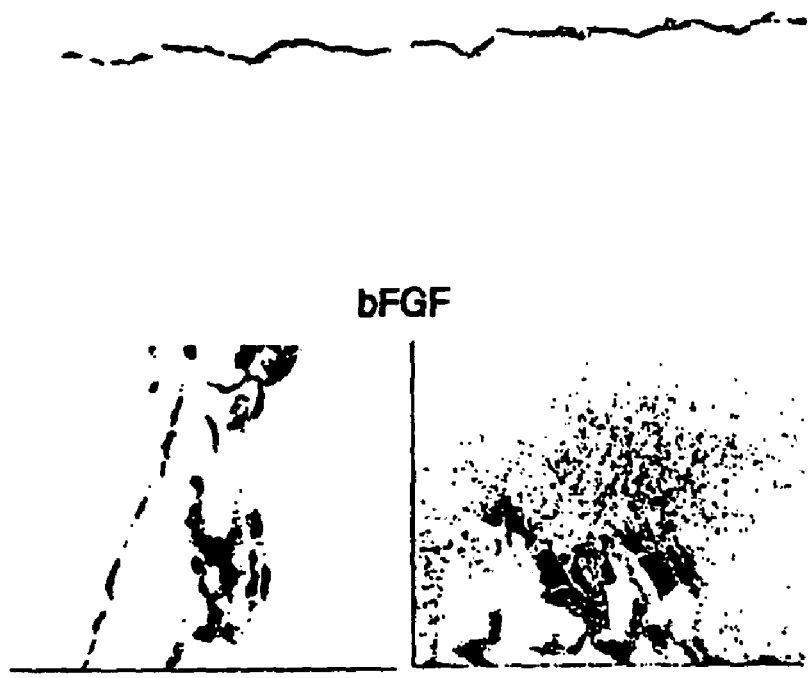
FIG. 5(B) depicts hematoxylin and eosin-stained cross-sections of the fibrin gel cultures. EC cells in untreated and TWEAK-treated cultures remain on the fibrin gel surface. Invading EC cord-like structures are shown in bFGF-treated cultures and structural organization of endothelial lumens in TWEAK+bFGF-treated cultures. Similar results were obtained with four independent EC types.
Figure 5B:
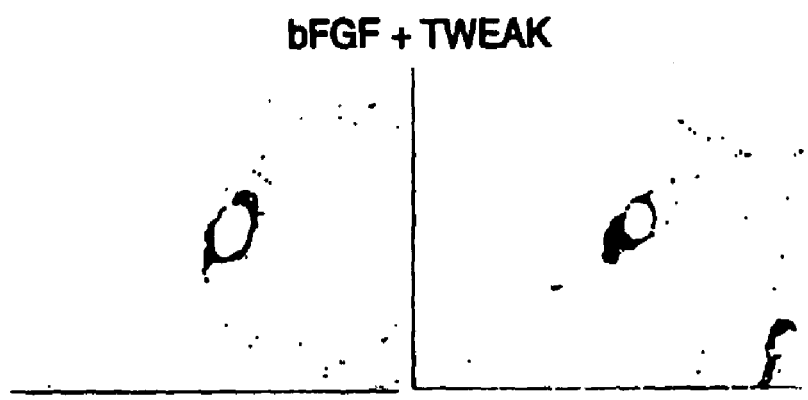
Figure 6:
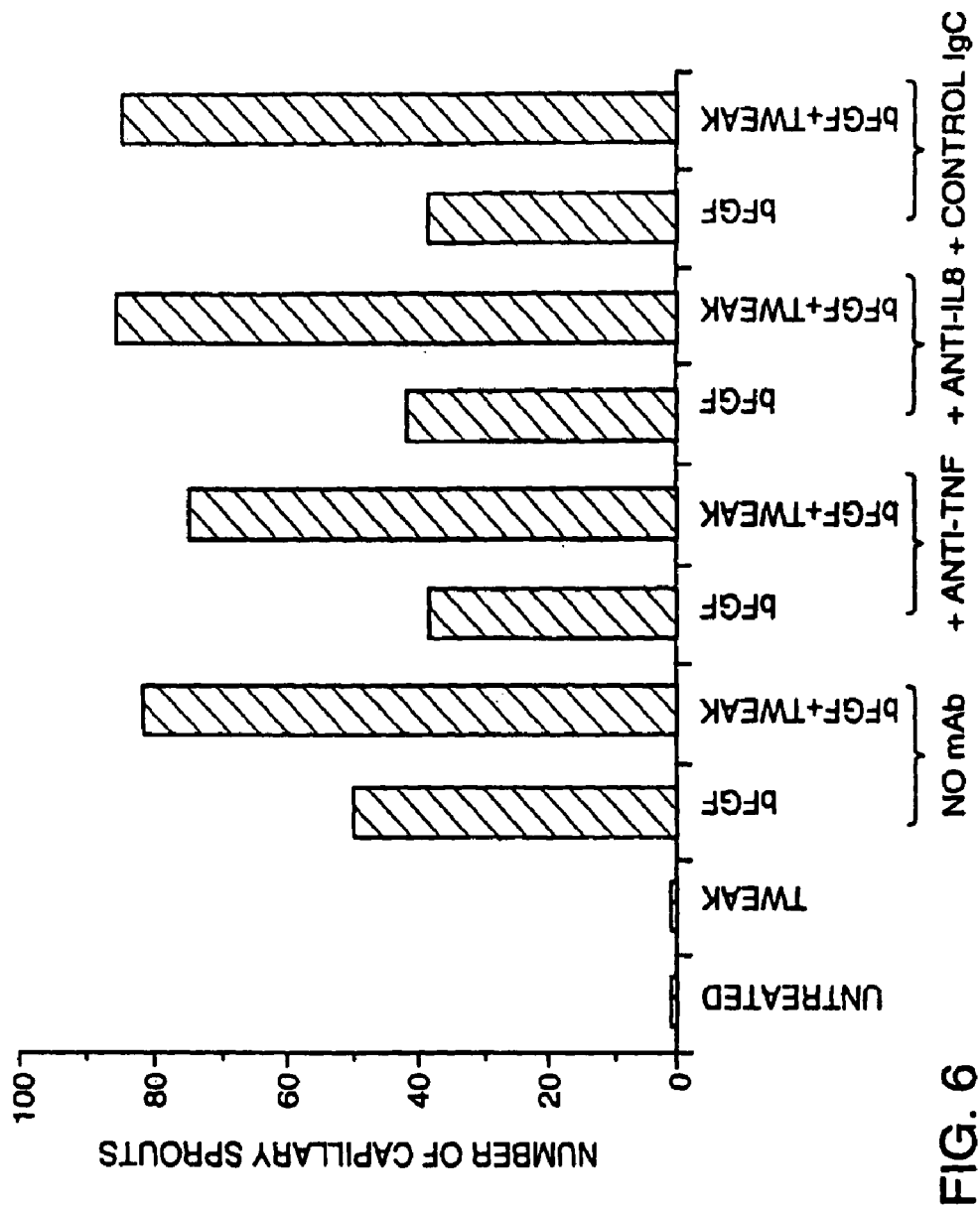
FIG. 6 depicts a bar graph showing the member of capillary sprouts after treatment with TWEAK and bFGF. HUVECS were plated on fibrin gel matrices and cultured for 48 hours without treatment, or with factors and anti-TNF and anti-IL-8 mAbs as indicated. Capillary sprouts were counted visually using five fields per well and the total number per culture shown. These results are representative of four independent experiments.

TWEAK differentially regulates EC morphogenesis induced by bFGF and VEGF—The growth of microvessels involves the coordinated proliferation, migration and morphogenetic organization of ECs into capillary tubes. The effect of TWEAK on morphogenic activity was assessed using cultures of EC seeded onto the surface of fibrin gels in the presence or absence of bFGF or VEGF. We found that bFGF but not TWEAK induced morphological changes in the EC monolayer on the fibrin gel surface as evidenced by phase-contrast microscopy (FIG. 5A) and that the addition of TWEAK to bFGF significantly enhanced these morphogenic changes, inducing a two-fold increase in the number of capillary sprouts (FIG. 6). Furthermore, histological analysis of cross-sections perpendicular to the matrix surface revealed that bFGF but not TWEAK promoted EC invasion into the fibrin matrix and that addition of TWEAK to bFGF induced the formation of lumen-containing structures (FIG. 5B). Similar results were obtained with several different EC types, including HUVECs, HDMEC, Human Pulmonary Artery EC, and Human Lung Microvascular EC, and no stimulation of lumen morphogenesis was observed when TWEAK was substituted for by another TNF family member, CD40L (data not shown). The cooperation between TWEAK and bFGF could be due to the ability of TWEAK to induce IL-8 (Chicheportiche, Y. et al., *J Biol Chem,* 272(51):32401 (1997)) and/or TNF (Schneider, P. R. et al., *Eur J Immunol,* 29(6):1785 (1999)), cytokines previously shown to cooperatively promote EC morphogenesis in vitro (Yoshida, S. et al., *Mol Cell Biol,* 17(7):4015 (1997); Koolwijk, P. et al., *The J. of Biol. Chem.,* 132:1177 (1996)). However, as shown in FIG. 6, the number of capillary sprouts formed by TWEAK+bFGF was not reduced in the presence of neutralizing mAbs for these factors. The inhibitory activity of these mAbs was independently confirmed, anti-TNF mAb inhibiting tumor killing and anti-IL-8 inhibiting IL-8-induced EC proliferation (data not shown).

Figure 7:
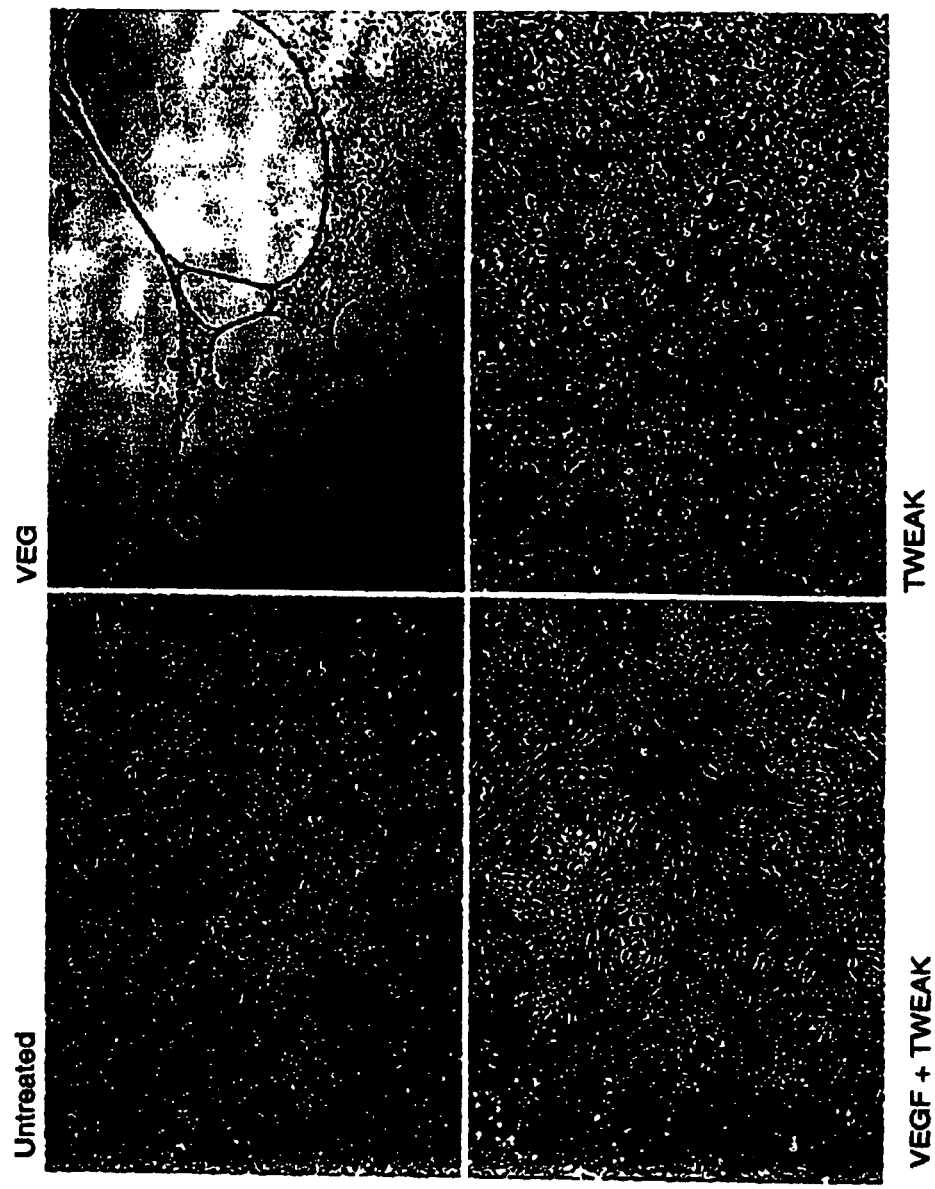
FIG. 7 depicts phase contrast images of HUVECs on the surface of fibrin gel matrices after 3 days of culture, untreated or treated with VEGF, TWEAK or TWEAK+VEGF. All images are 4× magnification.

VEGF also induced EC morphogenesis, as evidenced by the reorganization of the HUVEC monolayer on the fibrin gel surface (FIG. 7). The appearance of the structures induced by VEGF were qualitatively different from those induced by bFGF and there was no EC invasion into the fibrin matrix. Interestingly, confluent EC monolayers treated with TWEAK+VEGF did not reorganize, and were similar in appearance to untreated cultures and cultures treated with TWEAK alone. Thus TWEAK cooperates with bFGF to induce the formation of capillary-like structures but antagonizes the morphogenic response of HUVECs to VEGF.

Figure 8:
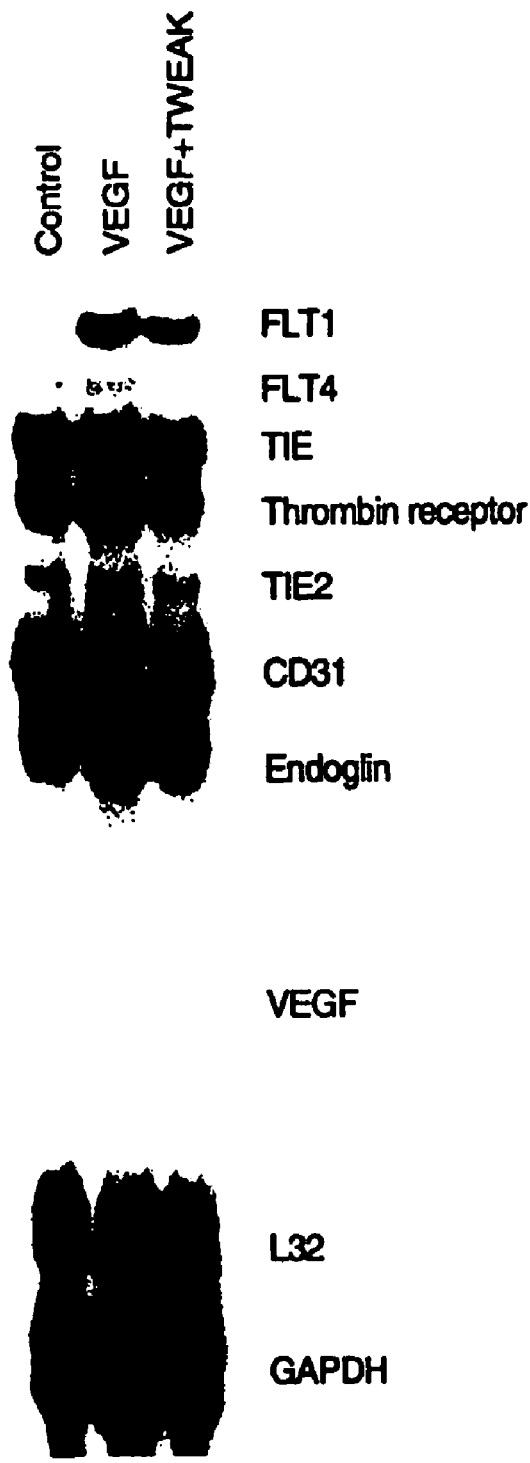
FIG. 8 is a gel electrophoresis image showing VEGF receptor FLT1 mRNA levels are decreased in cultures treated with TWEAK+VEGF as compared to cultures treated with VEGF alone.

TWEAK inhibits expression of VEGF receptor FLT1— TWEAK may regulate EC responses to VEGF by modulating VEGF signaling through its receptors. RPA expression analysis on a panel of angiogenic cytokines and receptors was performed as a means to address this possibility. Our results (FIG. 8) show an increase in the expression of FLT1 in cultures treated with VEGF as compared to control cultures. Cultures treated with TWEAK alone were similar to controls (data not shown). Interestingly, this response was inhibited in cultures treated with TWEAK+VEGF. Thus, TWEAK decreased mRNA levels of FLT1 in the presence of VEGF. Our RPA analysis also reveals inhibition by TWEAK of the expression of TIE, another EC receptor required for angiogenesis (Sato, T. N., et al., *Nature,* 376(6535):70-74 (1995)). These data suggest a mechanism whereby TWEAK may modulate signal transduction by angiogenic factors.

Accordingly, these results show that TWEAK antagonizes the morphogenic response of ECs to VEGF and inhibits VEGF-induced EC migration, but has no measurable effect on EC proliferation in the presence of VEGF, and the action of TWEAK may be pro-angiogenic or anti-angiogenic, depending upon the particular angiogenic context.

In contrast with the pro-angiogenic activity of TWEAK in the context of bFGF, these results show that TWEAK can inhibit the angiogenic behavior of ECs in other settings. TWEAK inhibits EC morphogenesis induced by VEGF, as evidenced by little if any change in the appearance of confluent EC monolayers plated onto fibrin gel surfaces in the presence of both factors. This anti-angiogenic effect of TWEAK may reflect TWEAK inhibition of VEGF-dependent EC migration which was observed independently in the wound repair assay. There was no changes in expression of the integrins $\alpha_v$, $\alpha_1$, $\alpha_2$, $\alpha_5$, $\beta_3$ and $\beta_1$, in cultures treated with TWEAK and VEGF as compared to VEGF alone (A. Jakubowski, unpublished observations). However, we found that the inducible expression of the VEGF receptor Flt-1 was inhibited by addition of TWEAK. Thus TWEAK may limit EC responses to VEGF by modulating VEGF signaling through its receptor. This is especially important in understanding and effecting tumor biology, where the role of endogenous VEGF is critical to tumor progression (Ferrars, N. and Davis-Smyth, T., *Endocrine Reviews,* 18:4-25 (1997)).

This data together with the TNF paradigm support the hypothesis that TWEAK can differentially modulate angiogenesis depending upon the particular angiogenic setting. These results indicate that it plays a role in the regulation of microvascular growth, remodeling, and/or maintenance in vivo, being pro-angiogenic or anti-angiogenic depending on the angiogenic context. Agonists (or antagonists) of the TWEAK pathway can provide useful therapeutic approaches to treatment in settings of ischemic injury, cancer, angioproliferative and inflammatory disorders.

Example 2

Growth of Lewis Lung Carcinoma is Inhibited in TWEAK-Transgenic (Tg) Mice

The Lewis Lung Carcinoma in vitro cell line was obtained from the Tumor Repository, NCI—Frederick Cancer Research and Development Center. The cell line was passed in vitro four passages in RPMI-1640/10% FBS without antibiotics prior to implantation into animals. The tumor cells (of C57BL/6 mouse strain origin) were injected at an innoculum of 1×106 cells per mouse subcutaneously in the right flank area of TWEAK-Tg mice and NonTg littermates which had been successively bred onto a C57BL/6 background. In each experiment, tumor cells were injected into 8 TWEAK-Tg mice and 8 NonTg littermates. Tumor measurements were recorded twice weekly and the average tumor weight at each time point calculated for each experimental group. Plots of tumor weight vs. time for each of two individual experiments are shown in FIG. 9, indicating that tumor growth was slower in mice expressing TWEAK as compared to their normal littermates.

TABLE I

TWEAK Binding to Primary Cell Types

| | TWEAK Binding[a] |
|---|---|
| Human Cell Types | |
| HUVEC | +++ |
| Aortic EC | ++ |
| Aortic Smooth Muscle Cells | +++ |
| Lung Fibroblasts | + |
| Embryonic Myoblasts | ++ |

TABLE I-continued

TWEAK Binding to Primary Cell Types

| | TWEAK Binding[a] |
|---|---|
| Peripheral Blood Lymphocytes | − |
| Peripheral Blood Dendritic Cells | − |
| Murine Cell Types | |
| EC cell line (MS-1) | ++ |
| Bone marrow fibroblast line (M210B4) | + |
| Spleen cells with and without anti-CD3 mAb activation | − |
| Lymph node cells with and without anti-CD3 mAb activation | − |
| Thymocytes with and without anti-CD3 mAb activation | − |
| Resident Peritoneal Macrophages | − |
| Thioglycollate-induced Macrophages (with and without LPS, TNF or IFNα stimulation) | − |

[a]Relative Binding compared to HUVECs as measured by immunofluorescent staining

The invention claimed is:

1. A method of inhibiting tumor progression in a subject, the method comprising administering to a subject having a tumor expressing Fn14 a therapeutically effective amount of an anti-Fn14 agonist antibody that binds human Fn14 and augments Fn14 signaling.

2. The method of claim 1, wherein the antibody is a monoclonal antibody.

3. The method of claim 1, wherein the antibody is a humanized antibody.

4. The method of claim 1, wherein the antibody is a chimeric antibody.

5. The method of claim 1, wherein the antibody is fully human.

6. The method of claim 1, wherein the antibody is primatized.

7. The method of claim 1, wherein the antibody is multivalent.

8. The method of claim 1, wherein the antibody is an IgG.

9. The method of claim 1, wherein the antibody is an IgM.

10. The method of claim 1, wherein the antibody is administered via the parenteral, intravenous, subcutaneous, intraperitoneal or intracapsular route.

11. The method of claim 1, wherein the antibody is administered in combination with radiation or chemotherapy.

12. A method of inducing tumor cell death in a subject, the method comprising administering to a subject having a tumor expressing Fn14 a therapeutically effective amount of an anti-Fn14 agonist antibody that binds human Fn14 and augments Fn14 signaling.

13. The method of claim 12, wherein the antibody is a monoclonal antibody.

14. The method of claim 12, wherein the antibody is a humanized antibody.

15. The method of claim 12, wherein the antibody is a chimeric antibody.

16. The method of claim 12, wherein the antibody is fully human.

17. The method of claim 12, wherein the antibody is primatized.

18. The method of claim 12, wherein the antibody is multivalent.

19. The method of claim 12, wherein the antibody is an IgG.

20. The method of claim 12, wherein the antibody is an IgM.

21. The method of claim 12, wherein the antibody is administered via the parenteral, intravenous, subcutaneous, intraperitoneal or intracapsular route.

22. The method of claim 12, wherein the antibody is administered in combination with radiation or chemotherapy.

23. A method of treating a cancer in a subject, the method comprising administering to a subject having a cancer expressing Fn14 a therapeutically effective amount of an anti-Fn14 agonist antibody that binds human Fn14 and augments Fn14 signaling.

24. The method of claim 23, wherein the antibody is a monoclonal antibody.

25. The method of claim 23, wherein the antibody is a humanized antibody.

26. The method of claim 23, wherein the antibody is a chimeric antibody.

27. The method of claim 23, wherein the antibody is fully human.

28. The method of claim 23, wherein the antibody is primatized.

29. The method of claim 23, wherein the antibody is multivalent.

30. The method of claim 23, wherein the antibody is an IgG.

31. The method of claim 23, wherein the antibody is an IgM.

32. The method of claim 23, wherein the antibody is administered via the parenteral, intravenous, subcutaneous, intraperitoneal or intracapsular route.

33. The method of claim 23, wherein the antibody is administered in combination with radiation or chemotherapy.

* * * * *

SEQUENCE LISTING

<160> NUMBER OF SEQ ID NOS: 2

<210> SEQ ID NO 1
<211> LENGTH: 129
<212> TYPE: PRT
<213> ORGANISM: Homo sapiens

<400> SEQUENCE: 1

```
Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
             20                  25                  30

Thr Ala Pro Cys Ser Arg Gly Ser Ser Trp Ser Ala Asp Leu Asp Lys
         35                  40                  45

Cys Met Asp Cys Ala Ser Cys Arg Ala Arg Pro His Ser Asp Phe Cys
     50                  55                  60

Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                 85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
            115                 120                 125

Gln
```

<210> SEQ ID NO 2
<211> LENGTH: 129
<212> TYPE: PRT
<213> ORGANISM: Mus musculus

<400> SEQUENCE: 2

```
Met Ala Pro Gly Trp Pro Arg Ser Leu Pro Gln Ile Leu Val Leu Gly
  1               5                  10                  15

Phe Gly Leu Val Leu Met Arg Ala Ala Ala Gly Glu Gln Ala Pro Gly
             20                  25                  30

Thr Ser Pro Cys Ser Ser Gly Ser Ser Trp Ser Ala Asp Leu Asp Lys
```

-continued

```
                35                    40                       45
Cys Met Asp Cys Ala Ser Cys Pro Ala Arg Pro His Ser Asp Phe Cys
    50                      55                  60

Leu Gly Cys Ala Ala Ala Pro Pro Ala His Phe Arg Leu Leu Trp Pro
65                      70              75                      80

Ile Leu Gly Gly Ala Leu Ser Leu Val Leu Val Leu Ala Leu Val Ser
                85                      90                  95

Ser Phe Leu Val Trp Arg Arg Cys Arg Arg Glu Lys Phe Thr Thr
                100                 105             110

Pro Ile Glu Glu Thr Gly Gly Glu Gly Cys Pro Gly Val Ala Leu Ile
        115                     120                 125

Gln
```